(12) United States Patent
Chatterjee

(10) Patent No.: US 9,376,369 B2
(45) Date of Patent: Jun. 28, 2016

(54) ANTI-CHOLESTEROLEMIC COMPOUNDS AND METHODS OF USE

(71) Applicant: Subroto Chatterjee, Columbia, MD (US)

(72) Inventor: Subroto Chatterjee, Columbia, MD (US)

(*) Notice: Subject to any disclaimer, the term of this patent is extended or adjusted under 35 U.S.C. 154(b) by 0 days.

(21) Appl. No.: 13/946,558

(22) Filed: Jul. 19, 2013

(65) Prior Publication Data

US 2014/0031304 A1 Jan. 30, 2014

Related U.S. Application Data

(63) Continuation of application No. 12/488,965, filed on Jun. 22, 2009, now Pat. No. 8,492,351, which is a continuation of application No. PCT/US2007/088780, filed on Dec. 24, 2007.

(60) Provisional application No. 60/876,761, filed on Dec. 22, 2006, provisional application No. 60/876,599, filed on Dec. 22, 2006, provisional application No. 60/877,753, filed on Dec. 29, 2006, provisional application No. 60/877,740, filed on Dec. 29, 2006.

(51) Int. Cl.

| | |
|---|---|
| *A23L 1/30* | (2006.01) |
| *A61K 31/235* | (2006.01) |
| *A61K 31/7024* | (2006.01) |
| *A61K 45/06* | (2006.01) |
| *C07C 69/84* | (2006.01) |
| *C07H 13/08* | (2006.01) |

(52) U.S. Cl.
CPC .............. *C07C 69/84* (2013.01); *A23L 1/3002* (2013.01); *A61K 31/235* (2013.01); *A61K 31/7024* (2013.01); *A61K 45/06* (2013.01); *C07H 13/08* (2013.01); *A23V 2002/00* (2013.01)

(58) Field of Classification Search
None
See application file for complete search history.

(56) References Cited

U.S. PATENT DOCUMENTS 5,260,335 A * 11/1993 Wagner et al. ................. 514/532
5,266,319 A * 11/1993 Cheng et al. .................... 514/23

FOREIGN PATENT DOCUMENTS

| WO | WO-2004/058213 A1 | 7/2004 | |
|---|---|---|---|
| WO | WO 2006022502 A1 * | 3/2006 | ........... A61K 31/216 |

OTHER PUBLICATIONS

Muruganandam et al. Indian Journal of Experimental Biology, vol. 40, Oct. 2002, pp. 1151-1160.*
Wang et al. Journal of Ethnopharmacology 96 (2005) 483-487, published online Nov. 11, 2004.*
Conner et al. Nutrition 12:274-277, 1996.*
Definition of Inflammation by Medical dictionary, http://medical-dictionary.thefreedictionary.com/Inflammation, internet article downloaded Sep. 22, 2015.*
Chae, Hypertension, 2001; 38:399-403.*
Abe I et al. "Potent and selective inhibition of squalene epoxidase by synthetic galloyl esters." Biochem Biophys Res Commun. Apr. 2, 2000;270(1):137-40.
Alzheimer's Disease—downloaded Jun. 2011 from PubMed Health.
American Heart Association, Cholesterol Abnormalities & Disease—downloaded Jun. 2011.
Baker, State University of New York at Buffalo Reporter, vol. 28, No. 35: Jul. 24, 1997.
Crespy V et al. "A review of the health effects of green tea catechins in in vivo animal models." J Nutr. Dec. 2004;134(12 Suppl):3431S-3440S.
Definition of food—dlownloaded from biology-online.org_<http://biology-online.org>, Jun. 2011.
Merck Manuals Online: Stroke—downloaded Jun. 2011.
Murase T et al. "Gallates inhibit cytokine-induced nuclear translocation of NF-kappaB and expression of leukocyte adhesion molecules in vascular endothelial cells." Arterioscler Thromb Vasc Biol. Jun. 1999;19(6):1412-20.
Muruganandam AV et al. "Effect of poly herbal formulation, EuMil, on chronic stress-induced homeostatic perturbations in rats." Indian J Exp Biol. Oct. 2002;40(10):1151-60. Abstract Only.
Okabe S et al. "New TNF-alpha releasing inhibitors, geraniin and corilagin, in leaves of Acer nikoense, Megusurino-ki." Biol Pharm Bull. Oct. 2001;24(10):1145-8.
Okuda et al., In Phenolic Compounds in Food and Their Effects on Health II; ACS Symposium Series; American Chemical Society: Washington, DC, 1992.
Tongia et al. Indian Journal of Indigenous Medicines, Oct. 1995; 17(2): 13-24, abstract only.
Kim et al. Influence of amla (Emblica officinalis Gaertn.) on hypercholesterolemia and lipid peroxidation in cholesterol-fed rats. J Nutr Sci Vitaminol (Tokyo). Dec. 2005;51(6):413-8.
Mathur et al. Hypolipidaemic effect of fruit juice of Emblica officinalis in cholesterol-fed rabbits. J Ethnopharmacol. Feb. 1996;50(2):61-8.
Thakur et al. The Ayurvedic medicines Haritaki, Amala and Bahira reduce cholesterol-induced atherosclerosis in rabbits. Int J Cardiol. Nov. 1988;21(2):167-75.
Zhang et al. Antiproliferative activity of the main constituents from Phyllanthus emblica. Biol Pharm Bull. Feb. 2004;27(2):251-5.

* cited by examiner

*Primary Examiner* — Layla Berry
(74) *Attorney, Agent, or Firm* — Mintz Levin Cohn Ferris Glovsky and Popeo, P.C.; Peter F. Corless, Esq.; Daniel W. Clarke

(57) ABSTRACT

The present invention provides novel compounds with hypocholesteremic activity from crude *Embilica officinialis* (EO) extracts and methods of use. The invention also provides nutraceuticals.

13 Claims, 11 Drawing Sheets

ANTI-CHOLESTEROLEMIC COMPOUNDS AND METHODS OF USE

RELATED APPLICATIONS

This application is a continuation of U.S. application Ser. No. 12/488,965, filed Jun. 22, 2009 (now U.S. Pat. No. 8,492, 351), which is a continuation of International Application No. PCT/US2007/088780 (WO 2008/080162) filed Dec. 24, 2007, which claims the benefit of U.S. Provisional Application 60/876,761 filed Dec. 22, 2006, U.S. Provisional Application 60/877,753 filed Dec. 29, 2006, U.S. Provisional Application 60/876,599 filed Dec. 22, 2006 and U.S. Provisional Application 60/877,740 filed Dec. 29, 2006. The entire contents of the aforementioned applications are hereby incorporated herein by reference.

GOVERNMENT SUPPORT

This invention was made with support from the United States Government under grant DK-31771 and DK-31722. The US Government has certain rights in this invention.

FIELD OF THE INVENTION

The present invention provides novel compounds with hypocholesteremic activity from *Embilica officinalis* (EO) extracts and methods of use. The invention provides nutraceuticals. The invention relates to the determination of the biological activity and mechanism of action by which the purified compounds lower cholesterol levels.

BACKGROUND OF THE INVENTION

According to the American Heart Association, an estimated 100,870,000 American adults have total cholesterol levels in the borderline-high risk range of 200 mg/dl to 239 mg/dl, and there are 40,600,000 American adults living with high-risk cholesterol levels of 240 mg/dl or more. There are many risk factors that can indicate a propensity to have high levels of cholesterol, such as age, weight, and health conditions such as diabetes, smoking, gender, race and ethnicity.

Hypercholesterolemia, or elevated blood cholesterol levels due to concentration of cholesterol in the cells and plasma, is an important risk factor definitively connected with potentially deadly cardiovascular disease, including atherosclerosis, coronary artery insufficiency, coronary heart disease, myocardial infarction and stroke. Millions of people around the world suffer from coronary heart disease, and it is the leading cause of death and morbidity at a productive age, especially in Western Europe and in the United States. Accordingly, cardiovascular disease presents a significant drain on healthcare resources in the western world. In the United States, total costs (direct and indirect) connected with the disease were estimated as about $118 billion in 2000; for 1.1 million citizens that experienced myocardial infarction, more than 40% of those died [Terry A. Jacobson, Clinical Context: Current Concepts of Coronary Heart Disease Management, Am J. Med. 2001; 110 (6A):3S-11S]. In addition, cardiovascular disease is growing at an alarming rate in Asian countries, and in particular among Asian Indians where cardiovascular disease has reached epidemic proportions [1].

Cholesterol (and its derivatives) biosynthesis underlies cardiovascular disease and, accordingly, inhibitors of cholesterol biosynthesis are a major focus of research efforts towards new therapeutics for cardiovascular disease. For a number of years, significant research was aimed at the development of competitive inhibitors for 3-hydroxy-3-methylglutaryl coenzyme A reductase, a major regulatory enzyme of cholesterol biosynthesis. Many attempts to use for this purpose oxygenated sterols, which via binding oxysterol receptors were expected to decrease activity of HMG-CoA reductase, did not bring practical results. A series of fungal metabolites with very high affinities for HMG-CoA reductase were found to be highly efficient inhibitors of cholesterol biosynthesis. These compounds and some synthetic analogs are commonly known as statins, are available commercially, and are widely used.

Although being relatively safe and efficient in treatment and prevention of coronary heart disease, statins have certain limitations in their use because of possible deleterious side effects, such as muscle weakness, and renal failure. Statin therapy is contra-indicated in pregnant women and patients with liver disorders. Additionally, there is a significant patient population in whom statins are not effective, and so the need for an agent that will lower cholesterol extends beyond the number of patients currently taking statins to lower their cholesterol levels. Taking additionally into account the relatively high costs of statin therapy, which varies from $20,000 to $40,000 per quality-adjusted life-year saved [John A. Farmer, Economic Implications of Lipid-Lowering Trials: Current Considerations in Selecting a Statin, Am J Cardiol 1998; 82:26 M-31M], and the desirability of long-term permanent treatment [Terry A. Jacobson, Clinical Context: Current Concepts of Coronary Heart Disease Management, Am J. Med. 2001; 110 (6A):3S-11S], it is evident that new agents are needed with similar targeting as the statins but with higher potency, safety, and availability and that will provide significant cost savings.

Accordingly, the instant invention provides novel compounds with anticholesterolemic activity, and methods of use.

SUMMARY

The present invention relates generally to methods and compositions for reducing hypercholesteremia in a subject. The invention is based on the identification of novel compounds from crude *Embilica officinialis* (EO) extracts. The invention relates to the determination of the biological activity and mechanism of action by which the purified compounds lower cholesterol levels. The invention provides nutraceuticals.

In a first aspect, the invention provides a method for preventing or treating an elevated blood lipid level-related disease or disorder in a subject comprising administering to the subject an effective amount of one or more gallic acid derivatives, thereby preventing or treating an elevated blood lipid level-related disease or disorder in the subject.

In another aspect, the invention provides a method for preventing or treating inflammation in a subject comprising administering to the subject an effective amount of one or more gallic acid derivatives, thereby preventing or treating inflammation in the subject.

In still another aspect, the invention provides a method for preventing or treating a stress response in a subject comprising administering to the subject an effective amount of one or more gallic acid derivatives, thereby preventing or treating a stress response in the subject.

In one embodiment of any one of the above aspects, the one or more gallic acid derivatives is administered as a nutraceutical.

In one aspect, the present invention provides a nutraceutical comprising one or more gallic acid derivatives.

In a further aspect, the present invention provides a nutraceutical comprising one or more extracts from EuMil.

In another embodiment of any one of the above aspects, the one or more gallic acid derivatives are selected from the group consisting of: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

In another particular embodiment, the one or more gallic acid derivatives are selected from the group consisting of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

In still another embodiment, the elevated blood lipid level-related disease or disorder is selected from the group consisting of: hyperlipidemia, arteriosclerosis, fatty liver, angina pectoris, stroke, Alzheimer's disease, obesity, diabetes, arthritis, and inflammatory diseases.

In another aspect, the invention features a method of reducing cholesterol biosynthesis in a subject comprising administering an effective amount of one or more gallic acid derivatives, thereby reducing cholesterol biosynthesis in a subject.

In another aspect, the invention features a method of increasing the cellular efflux of cholesterol in a subject comprising administering an effective amount of one or more gallic acid derivatives, thereby increasing the cellular efflux of cholesterol in a subject.

In another particular aspect, the invention features a method of inhibiting the cellular uptake of cholesterol in a subject comprising administering an effective amount of one or more gallic acid derivatives, thereby inhibiting the cellular uptake of cholesterol in a subject.

In still another aspect, the invention features a method of inhibiting the oxidation of LDL, comprising administering an effective amount of one or more gallic acid derivatives, thereby preventing the oxidation of LDL.

In one embodiment of any one of the above-mentioned aspects, the one or more gallic acid derivatives is administered as a nutraceutical.

In another embodiment of any one of the above mentioned aspects, the one or more gallic acid derivatives are selected from the group consisting of: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

In a further particular embodiment, the one or more gallic acid derivatives are selected from the group consisting of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

In another embodiment of any of the aspects as set forth above, the at least one gallic acid derivative is present in an amount from about 10 mg-500 mg. In a further related embodiment, the at least one gallic acid derivative is present in an amount from about 40 mg-200 mg.

In another embodiment of any one of the aspects as set forth above, the method comprises administering at least one or more second agents. In a further embodiment, the one or more second agents is a therapeutic agent.

In a particular embodiment, the therapeutic agent is selected from the group consisting of inhibitors of cholesterol metabolism, inhibitors of triglyceride synthesis, beta blockers, diuretics, inhibitors of platelet aggregation, angiogenesis inhibitors angiogenesis inhibitors, arthritis medication, toxins, anti-inflammatory agents. In a related embodiment, the therapeutic agent is attached to the gallic acid derivative by a covalent linkage.

In a further embodiment, the therapeutic agent is administered in combination with the one or more gallic acid derivatives.

In another aspect, the invention features a pharmaceutical composition for the treatment or prevention of an elevated blood lipid level-related disease or disorder comprising one or more gallic acid derivatives and a pharmaceutically acceptable excipient.

In one embodiment, the gallic acid derivative is derived from EuMil.

In another embodiment, the one or more gallic acid derivatives is selected from the group comprising: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

In another embodiment, the pharmaceutical composition comprises a combination of gallic acid derivatives selected from the group consisting of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

In a particular embodiment, the at least one gallic acid derivative is present in an amount from about 10 mg-500 mg. In a related embodiment, the at least one gallic acid derivative is present in an amount from about 40 mg-200 mg.

In another embodiment, the composition further comprises one or more second agents. In a related embodiment, the one or more second agents is a therapeutic agent.

In another embodiment, the therapeutic agent is selected from the group consisting of inhibitors of cholesterol metabolism, inhibitors of triglyceride synthesis, beta blockers, diuretics, inhibitors of platelet aggregation, angiogenesis inhibitors, arthritis medication, toxins, anti-inflammatory agents.

In a further embodiment, the therapeutic agent is attached to the gallic acid derivative by a covalent linkage.

In one embodiment of any one of the above-mentioned aspects, the composition is administered in a dosage form selected from the group consisting of a: food composition, tablet, pill, gel, patch, capsule, suspension tablet, liquid, aqueous emulsion powder, lozenge, sachet, cachet, elixir, suspension, emulsion, syrup, aerosol, ointment, soft gelatin capsule, and hard gelatin capsule, suppository, creams, lotions, solutions, gels, pastes powder, and suspension.

In a further embodiment, the food is a health food product, a food product made from cereal flour, gums, a dairy product, a soup, a broth, a paste, a sauce, a beverage, a vitamin complex, a food rich in cholesterol, salt, or pepper.

In another embodiment, the dosage form is further selected from the group consisting of immediate release, sustained release, and delayed release.

In a particular embodiment, the dosage comprises about 0.1% to about 95% gallic acid derivative weight to weight of the composition.

In another embodiment of any one of the above aspects, the subject is a mammal. In another related embodiment, the mammal is a human.

In another aspect, the invention features a kit for the use in preventing or treating an elevated blood lipid level-related disease in a mammal comprising one or more gallic acid derivatives.

In one embodiment, the one or more gallic acid derivatives is selected from the group comprising: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid, and instructions for use.

In another embodiment, the kit comprises a combination of gallic acid derivatives selected from the group consisting of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

In another aspect, the invention features a kit for the use in preventing or treating an elevated blood lipid level related disease or disorder in a subject comprising one or more gallic acid derivatives, and instructions for use.

In another aspect, the invention features a kit for the use in preventing or treating inflammation in a subject comprising one or more gallic acid derivatives, and instructions for use.

In still another aspect, the invention features a kit for the use in preventing or treating a stress response in a subject comprising one or more gallic acid derivatives, and instructions for use.

In another aspect, the invention features a kit for use in reducing cholesterol biosynthesis, increasing the cellular efflux of cholesterol, or inhibiting the cellular uptake of cholesterol comprising one or more gallic acid derivatives, and instructions for use.

In one embodiment of any one of the above-mentioned aspects, the one or more gallic acid derivatives is administered as a nutraceutical.

In another embodiment of any one of the above-mentioned aspects, the one or more gallic acid derivatives is selected from the group comprising: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid, and instructions for use.

In another embodiment, the invention features a kit comprising a pharmaceutical composition according to any one of the above-mentioned aspects, and instructions for use.

Each of the aspects described herein may be combined with one, more than one or all of the other aspects and features within each of the aspects may be combined with features from the other aspects.

Other aspects of the invention are described infra.

DETAILED DESCRIPTION OF THE INVENTION

Figure 1:
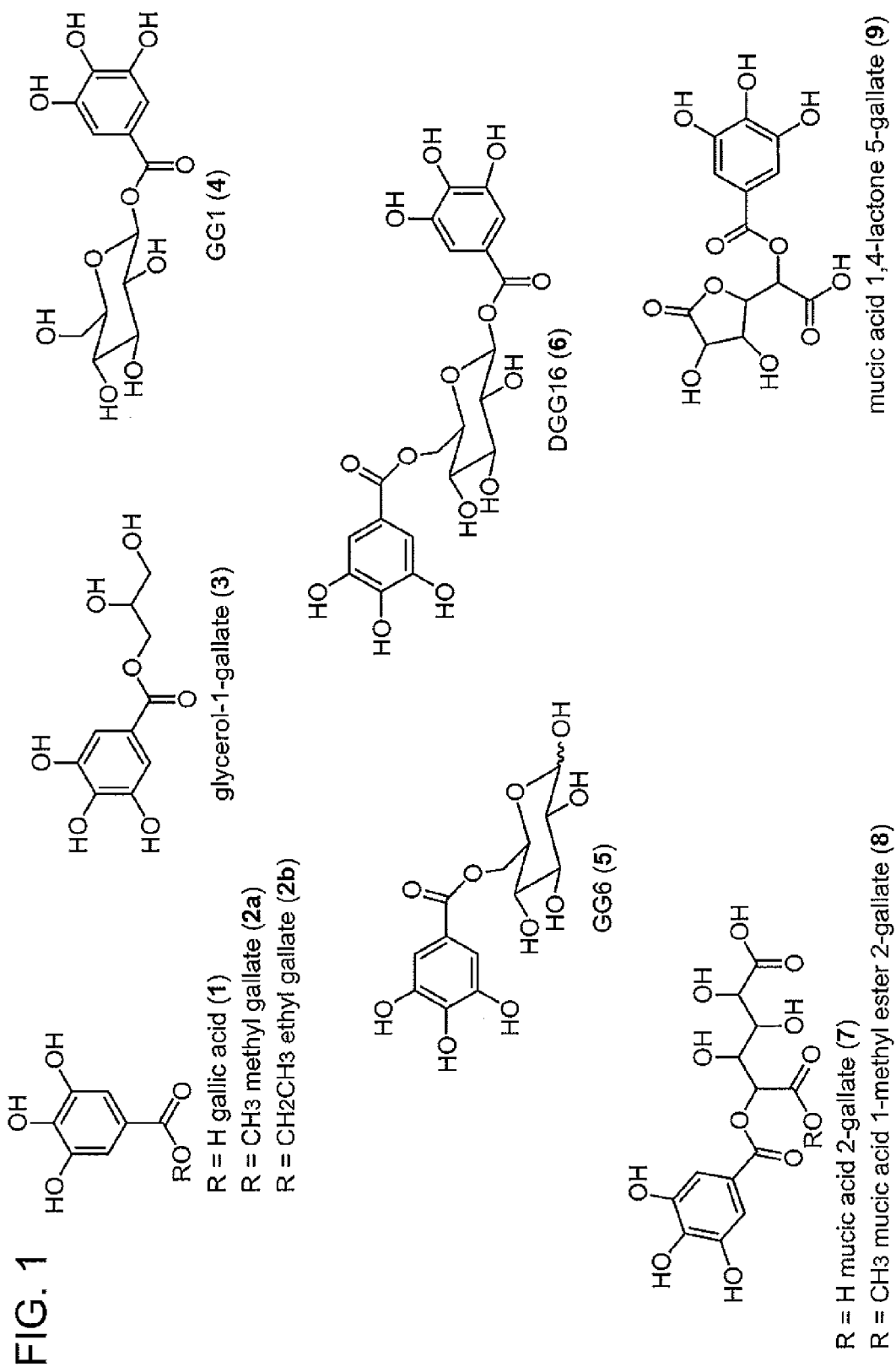
FIG. 1 shows the structures of active compounds isolated from the fruit of *Embilica officinalis* (EO).
Figure 1:
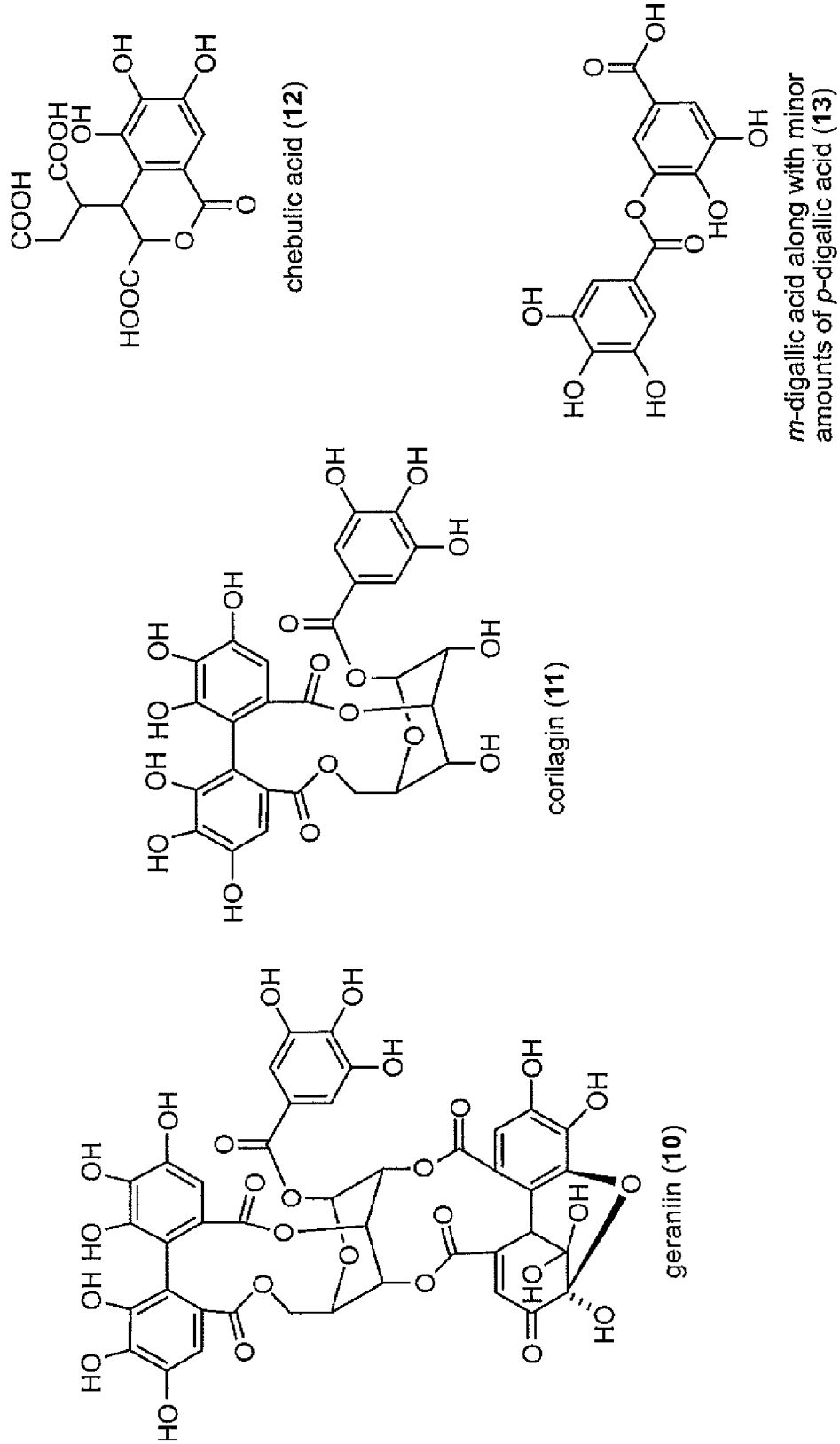

The present invention relates generally to methods and compositions for reducing hypercholesteremia in a subject. The invention is based on the identification of novel compounds from crude *Embilica officinialis* (EO) extracts. The invention relates to the determination of the biological activity and mechanism of action by which the purified compounds lower cholesterol levels and provides nutraceuticals.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the terms "therapeutically effective" or "amount sufficient" refers to when a composition or method of the invention is properly administered in vivo to a mammal, including humans, a measurable beneficial effect occurs. Exemplary beneficial effects include measurable reduction in the level of cholesterol and/or LDL and/or triglycerides in the blood of the mammal; reduction of clinically verifiable and/or patient-reported level of high cholesterol and/or LDL and/or triglycerides or complete resolution or curing of the elevated LDL and/or cholesterol and/or triglyceride condition or other diseases.

As used herein, the phrase "elevated lipid level-related disease or disorder" is meant to refer to any disease or disorder that is characterized by or is related to an elevated level of LDL or with elevated levels of total cholesterol. In certain preferred embodiments, an elevated blood lipid level related disease or disorder can be, but is not limited to, hyperlipidemia, arteriosclerosis, fatty liver, angina pectoris, stroke, alzheimer's disease, obesity, diabetes, arthritis, and inflammatory diseases.

The terms "hypercholesteremia" or "hypercholesterolemia" as used herein mean the presence of high levels of cholesterol in the blood of a mammal.

As used herein, the terms "concurrent" or "concurrent administration" mean that the EO composition and an agent, in certain embodiments a therapeutic agent, are administered to the subject either (a) simultaneously in time (optionally by formulating the two together in a common carrier), or (b) at different times during the course of a common treatment schedule. In the latter case, the two compounds are administered sufficiently close in time to achieve the intended effect.

As used herein, the term "gallic acid derivative" is meant to refer to a derivative of 3,4,5-Trihydroxybenzoic acid. In certain preferred embodiments, the gallic acid derivative is isolated from the fruit from *Embilica officinalis* (EO). In other preferred embodiments, the gallic acid derivatives are selected from compounds 2a-13.

As used herein, the term "stress response" is meant to refer to the ability of one or more gallic acid derivatives to lower the expression of a protein that is a marker of stress, for example, but not limited to, a heat shock protein. In certain embodiments, a stress response is measured by the ability of one or more gallic acid derivatives to lower the expression of heat shock protein 70 (Hsp70).

As used herein, the term "cholesterol efflux" is meant to refer to the ability of a compound to promote the release of cholesterol from cells.

As used herein, the term "EuMil" is meant to refer to a polyherbal formulation consisting of extracts of *Embilica officinalis Gaertn* (syn. *Phyllanthus embliica* Linn.) (EO), *Withania somnifera* (L) Dunal and *Ocimum sanctum* L with *Asparagus racemosus Willd* used as filler. In preferred embodiments, the extracts of EO, *Withania somnifera* (L) Dunal and *Ocimum* are used in equal portions.

As used herein, the phrase "in combination with" is intended to refer to all forms of administration that provide an inhibitory nucleic acid molecule together with a second agent, such as a second inhibitory nucleic acid molecule or a chemotherapeutic agent, where the two are administered concurrently or sequentially in any order.

As used herein, a "subject" is a vertebrate, preferably a mammal, more preferably a human. Mammals include, but are not limited to, murines, simians, humans, farm animals, sport animals, zoo animals and pets, for example cats, dogs, cattle, fish, birds. A subject can include a genetically compromised or genetically manipulated vertebrate, preferably a genetically compromised or genetically manipulated mammal, more preferably genetically compromised or genetically manipulated farm animals, sport animals, zoo animals or pets, for example cats, dogs, cattle, fish, birds.

The term "pharmaceutically-acceptable excipient" as used herein means one or more compatible solid or liquid filler, diluents or encapsulating substances that are suitable for administration into a human.

The term "nutraceutical" is meant to refer to any substance that is a food or a part of a food or something that is added to a food, and provides medical or health benefits, including the prevention and/or the treatment of a disease or disorder. Nutraceuticals are often natural products that are identified from botanicals, and purified or partially purified and then included in foods.

I. Cholesterol

Cholesterol is the principal sterol of humans and higher animals. Cholesterol is an important component of cell membranes and lipoproteins, and is a key biosynthetic precursor of bile acids and steroidal hormones. Cholesterol is found in all body tissues and also among the lipids in the bloodstream, but with especially high content in the brain, spinal cord and in animal fats. Nevertheless, an increased level of cholesterol in the blood, especially in its low-density lipoprotein-bound form, is the critical factor in the development of coronary heart disease, which creates a danger of heart attack.

Because of insolubility of cholesterol, it is transported in the blood in a modified form of lipoproteins. There are a number of lipoproteins differing in their properties and physiological role, but the most important are low-density lipoprotein (LDL) and high-density lipoprotein (HDL).

LDL is a major carrier of cholesterol in the blood and, as mentioned above, elevated LDL levels are a major risk factor in the development of coronary heart disease. Its excess in the blood leads to a situation when arteries are blocked to a greater or lesser extent by the deposition of cholesterol plaques that leads to a condition of stenosis or atherosclerosis in particular. Inflammation, hemodynamic factors and the like contribute to plaque rupture that, in turn, further contributes to thrombus formation, blocking blood flow in coronary or cerebral arterial vessels.

The following approximate values are generally considered optimal, near optimal, borderline, high and very high:

| | | |
|---|---|---|
| LDL Cholesterol (mg/dL) | <100 | Optimal |
| | 100-129 | Near optimal/above optimal |
| | 130-159 | Borderline high |
| | 160-189 | High |
| | >=190 | Very high |
| Total Cholesterol (mg/dL) | <200 | Desirable |
| | 200-239 | Borderline high |
| | >=240 | High |
| HDL Cholesterol (mg/dL) | <40 | Low |
| | >=60 | High |

The above recommendations are for individuals with moderate to high risk. Persons with very high risk such as established CVD plus multiple major risk factors, severe and poorly controlled risk factors, multiple risk factors of metabolic syndrome, acute coronary syndromes the goal is to have LDL-cholesterol below 70 mg/dL.

Typically, the average person consumes between 350-400 mg of cholesterol daily, while the recommended intake is around 300 milligrams. Increased dietary cholesterol consumption, especially in conjunction with a diet high in saturated fat intake, can result in elevated serum cholesterol. Having an elevated serum cholesterol level is a well-established risk factor for heart disease, and therefore there is a need to mitigate the undesired effects of cholesterol accumulation. High cholesterol levels are generally considered to be those total cholesterol levels at 200 milligrams and above, or LDL cholesterol levels at 130 milligrams and above. By lowering the total system LDL cholesterol level, it is believed that certain health risks, such as coronary disease and possibly some cancers that are typically associated with high cholesterol levels, can be reduced.

Numerous studies relating to modifying the intestinal metabolism of lipids illustrate that such effects can reduce a high cholesterol level (Burnett et al., Expert Opin Investig Drugs., 5(11):1337-51, 2006; Wang et al., Am J Physiol Gastrointest Liver Physiol., 287(3):G547-54, 2004; Heidrich et al., BMC Pharmacology, 4:5, 2004; Borel et al., Am. J. Clin. Nutr., 49:1192-1202, 1989; Malinow et al., Am. J. Clin. Nutr., 30:2061-2067, 1977). Hampering the absorption of triglycerides, cholesterol or bile acids, or a combination of these mechanisms, results in a lowering of cholesterol levels in the serum (Lewis et al., Journal of Lipid Research, 36:1098-1105, 1995). Also by interfering with the digestion of dietary phospholipids these compounds may affect a critical micelle formation and consequently the absorption of cholesterol.

Seminal studies by Steinberg et al. have demonstrated that LDL and ox-LDL are cytotoxic to cells of the vascular wall and may contribute to endothelial injury (23). The entry of ox-LDL into the sub-endothelial space and uptake by monocytes and aortic smooth muscle cells contribute to fatty streak formation. Alternatively, LDL taken up via pinocytic mechanism by the vascular endothelial cells allows LDL to enter the sub-endothelial space. Here depending upon the anti-oxidant status/level of the vascular wall the LDL may undergo oxidation. Such minimally oxidized LDL or fully ox-LDL is taken up by monocytes/smooth muscle cells leading to foam cell formation a "hallmark in the pathogenesis in atherosclerosis" (24). In addition, oxidized phospholipids components present in minimally oxidized lipoproteins such as 1-palmitoyl 2-(5-oxovaleroyl)phosphatidylcholine (POVPC) can stimulate the proliferation of aortic smooth muscle cells, contributing to intima/media thickening (25).

Human plasma LDL plays a major role in the delivery of cholesterol from hepatic tissue to extra-hepatic tissue through the LDL (Beta) receptor [3]. Nonetheless, elevated levels of plasma and LDL cholesterol promote atherosclerosis via an increased uptake through a LDL receptor-independent pathway. For example, previous studies have shown that modified LDL, upon oxidation or glycosylation, has a predilection for uptake through the LDL receptor-independent pathway. Thus ox-LDL taken by aortic smooth muscle cells and macrophages through the LDL receptor independent/scavenger pathway contributes to foam cell/fatty streak formation by stimulating cholesteryl ester accumulation and by inhibiting its degradation [4].

When the flow is directed to a part of the heart muscle, this can cause a heart attack. If a thrombus blocks the blood flow to a certain region of the brain, the consequence is a stroke.

In contrast to LDL, HDL carries the excess of cholesterol from tissues away to the liver. It is considered to be able to remove some cholesterol from atherosclerotic plaques thus making their growth slower. Angiographical studies showed a correlation between elevated levels of HDL and a decreased number of sites of stenosis in the coronary arteries of humans. This indicates a protective action of HDL against heart attack and indicates a possibility to use measuring HDL level as a prognostic indicator of higher or lower risk.

Demand of the body in cholesterol is covered by two sources: by the biosynthesis that mainly proceeds in the liver, intestine and skin, and via uptake from food, mainly from animal and dairy products. Under mixed diet, ratio of cholesterol amounts supplied by the sources is about 1:1.

Cellular cholesterol homeostasis is very important for the prevention of coronary heart disease. In general, the plasma concentration of cholesterol in the body is regulated by the dietary cholesterol absorption, by the biosynthesis of cholesterol itself and its esterified forms, by the metabolic removal of circulating cholesterol, and by the excretion of cholesterol via bile and feces, by cholesterol efflux from peripheral tissues via HDL and back to the liver for further metabolism.

Both diet and genetically determined biosynthetic-metabolic specificity of the body are instrumental in the development of atherosclerosis. A diet high in cholesterol will lead to a high level of cholesterol in the bloodstream, which has important consequences. Dietary cholesterol suppresses the biosynthesis of cholesterol in the body, especially in tissues other than the liver. A parallel effect is inhibition of synthesis of LDL receptors. As a result of reduction in the number of receptors, the level of LDL in blood increases, leading to the deposition of atherosclerotic plaques. Damaged biosynthesis of LDL receptors could be also a result of a genetic deviation. Thus, a good regulation of cholesterol biosynthesis is very important. Oxygenated derivatives of cholesterol seem to control the biosynthesis of the responsible enzymes in a receptor-mediated process, providing a feedback regulation for the biosynthesis of cholesterol. Thus, modern approaches to prevention of atherosclerosis are based on the correction of both external and internal factors ruling the cholesterol level in blood: dietary supply and absorption of exogenous cholesterol, on the one hand, and the biosynthesis of endogenous cholesterol and related structures, on the other hand.

Statins

In correcting internal factors, inhibitors of cholesterol (and its derivatives) biosynthesis play an important role and the search for new agents with this activity now constitutes a major research effort. For a number of years, significant research went into the development of competitive inhibitors for 3-hydroxy-3-methylglutaryl coenzyme A reductase, a major regulatory enzyme of cholesterol biosynthesis. Many attempts to use oxygenated sterols for this purpose, which via binding oxysterol receptors were expected to decrease activity of HMG-CoA reductase, did not bring practical results. A breakthrough came with the discovery of a series of fungal metabolites with very high affinities for HMG-CoA reductase which were found to be highly efficient inhibitors of cholesterol biosynthesis. Nowadays these compounds and some synthetic analogs, commonly known as statins, are available commercially and widely used.

Although being relatively safe and efficient in treatment and prevention of coronary heart disease, statins have certain limitations in their use and they need care in application because of possible side effects such as those provided below.

In mammalian cells, the rate-limiting step in cholesterol biosynthesis involves the conversion of hydroxymethylglutaryl co-enzyme A (HMG-CoA) to mevalonic acid through the enzyme HMG-CoA reductase. The widely prescribed statin, simvastatin (ZOCOR), inhibits HMG-CoA reductase activity and markedly reduces the blood levels of cholesterol as well as episodes of stroke and heart attacks [5, 6]. In as much as the collective group of statins can lower blood level of cholesterol, they may impart several adverse effects such as muscle weakness and renal failure, and are contra-indicated in pregnant women and patients with liver disorders. Thus, patients taking them respond very often to the lowering of cholesterol biosynthesis by a compensatory enhancement of cholesterol absorption from food and, especially for the cases when statins are used as a monotherapy, some patients fail to reach treatment goals. The risk of liver complications dictates the use of statins under medical control. Taking additionally into account the relatively high costs of statin therapy, which varies from $20,000 to $40,000 per quality-adjusted life-year saved [John A. Farmer, Economic Implications of Lipid-Lowering Trials: Current Considerations in Selecting a Statin, Am J Cardiol 1998; 82:26 M31M] and the desirability of long-term permanent treatment [Terry A. Jacobson, Clinical Context: Current Concepts of Coronary Heart Disease Management, Am J. Med. 2001; 110 (6A):3S-11S], it is evident that the new agents are needed with similar targeting as the statins but with higher potency, safety, availability and significant cost savings for patients, third party insurers, state and federal government payors as well.

There also exists a significant patient population in whom statins are not effective, so the need for an agent that will lower cholesterol extends beyond the number of patients currently taking statins to lower their cholesterol levels.

Other Cholesterol Modulating Agents

The uptake of dietary cholesterol by intestine and other tissues as well the cellular efflux of cholesterol also are key determinants of cholesterol homeostasis [7,8]. Accordingly, drugs that can collectively modulate multiple cholesterol homeostatic mechanisms have become available, such as VYTORIN, which is a mixture of ZETIA and ZOCOR/SIMVASTATIN. ZETIA inhibits the uptake of dietary cholesterol in intestinal epithelial cells while Simvastatin inhibits the activity of HMG-CoA reductase, that in turn further inhibits endogenous cholesterol biosynthesis. However, these drugs also have numerous side effects.

Torcetrapib an inhibitor of cholesterol ester transfer protein (CETP) is another class of compounds that lower blood levels of cholesterol by raising HDL cholesterol levels. CETP plays a role in the reverse cholesterol transport pathway as well as in the intravascular remodeling and recycling of HDL particles. CETP promotes the transfer of cholesteryl esters from beneficial antiatherogenic HDLs to proatherogenic apolipoprotein B-containing lipoproteins (e.g., LDL and very low-density lipoprotein cholesterol). When there is an excess of circulating concentrations of atherogenic lipoproteins relative to HDL, arterial cholesterol deposition and atherogenesis are greatly enhanced. Thus, high plasma levels of CETP are correlated with low HDL cholesterol levels. However, Torcetrapib has been withdrawn from the market because of deleterious effects in man. In general, the concept of CETP inhibitors as useful candidates is still viable and may be of use as a target to lower cholesterol in the invention as described herein.

Elevated Blood Lipid Level Related Diseases

The invention features, in certain embodiments, methods for preventing or treating an elevated blood lipid level-related disease or disorder. In certain embodiments, an elevated lipid level-related disease or disorder can refer to, but is not limited to, any disease or disorder that is characterized by or is related to an elevated level of LDL or with elevated levels of total cholesterol.

In certain preferred embodiments, an elevated blood lipid level related disease or disorder can be, but is not limited to, hyperlipidemia, arteriosclerosis, fatty liver, angina pectoris, stroke, Alzheimer's disease, obesity, diabetes, arthritis, and inflammatory diseases.

Although not limited to the following, preferred elevated lipid level-related diseases or disorders that can be treated by the methods of the invention include hypercholesterolemia, mixed hyperlipidemias, metabolic syndrome, hypo-alphaprotienemia, myocardial infarction, stroke, Alzheimer's disease, diabetes, and obesity, and post menopausal women.

Hypercholesteremia

Hypercholesterolemia is an important risk factor definitively connected with cardiovascular disease and, particularly, with atherosclerosis and coronary heart disease. Millions of people around the world suffer from coronary heart disease, which is the leading cause of death and morbidity in a productive age, especially in Western Europe and in the United States. For this reason it is also a significant drain on healthcare resources in the Western world. For example, in the USA total costs (direct and indirect) connected with the disease were estimated to be about $118 billion in 2000. For 1.1 million citizens that experienced myocardial infarction, more than 40% of those died [Terry A. Jacobson, Clinical Context: Current Concepts of Coronary Heart Disease Management, Am J. Med. 2001; 110 (6A):3S11S]. In addition, this disease is growing at an alarming rate in Asian countries particularly among Asian Indians where CVD has reached epidemic proportions [1]. Several established risk factors that contribute to CVD include elevated levels of blood cholesterol, homocysteine, high sensitive C-reactive proteins (hs-CRP), diabetes, stroke and stress [2].

Atherosclerosis

Atherosclerosis is the most common cause of death and serious morbidity in the Western world. Atherosclerosis is one of three morphologically distinct forms of arteriosclerosis. Arteriosclerosis is the hardening of the arteries due to their thickening and loss of elasticity. Atherosclerosis occurs when irregularly distributed lipid deposits in the inner coating of the vessels of the elastic arteries, such as the aorta, carotid and iliac, or the large and medium-sized muscular arteries, such as the coronary and popliteal. These lipid deposits, called atheromatous plaques, cause fibrosis and calcification, which leads to coronary heart disease and myocardial infarction. The plaques are comprised of cells, macrophages and other leukocytes, a connective tissue extra-cellular matrix and intracellular and extracellular lipid deposits. The progression of atherosclerosis can be slowed by reducing the plasma cholesterol and cholesterol LDL levels.

Cholesterol and its oxidized derivatives are thought to accumulate in atherosclerotic lesions when cholesterol influx exceeds efflux. This may provide an explanation for atherosclerosis in patients with lipid disorders.

Correcting external factors is realized via diet modification, such as reduction of dietary supply of cholesterol, for example by partial substitution of food animal fats by plant fats that do not contain cholesterol. The reduction of dietary cholesterol absorption can be reached via application of special food additives or foods enriched by the abundant phytosterols, such as beta-sitosterol or campesterol, or their saturated derivatives (stanols). Plant sterols produce anticholesterolemic effect which is considered to be connected with the inhibition of cholesterol absorption in the intestine because of competition with cholesterol for incorporation into micelles, although other absorption steps may also be involved. When the plant sterols replace cholesterol of the micelles, free cholesterol is excreted with feces. A limitation of the approach is that relatively large doses of sterols are required for modest reduction in plasma cholesterol. The same is true in respect to other agents blocking cholesterol absorption, such as stanols, aminoglycoside, the antibiotic neomycin, which appears to inhibit cholesterol absorption by forming complexes with cholesterol that are excreted, and the bile salt binder cholestyramine, an anion exchanger that indirectly alters cholesterol levels by limiting the resorption of cholesterol-derived bile salts.

Hyperlipidemia

Hyperlipidemia is an elevation of lipids (fats) in the bloodstream. These lipids include cholesterol, cholesterol esters (compounds), phospholipids and triglycerides. When hyperlipidemia is defined in terms of a class or classes of elevated lipoproteins in the blood, the term hyperlipoproteinemia is used. Hypercholesterolemia is the term for high cholesterol levels in the blood. Hypertriglyceridemia refers to high triglyceride levels in the blood. The American Heart Association provides information to the public on hyperlipidemia on the world wide web at americanheartorg/presenter.jhtml?identifier=4600.

Included are hyperlipidemias that are induced by other conditions or agents, for example HIV drug induced hypercholesterolemia/hyperlipidemia.

Fatty Liver

Fatty liver refers to the build-up of excess fat in the liver cells. It is normal for the liver to contain some fat; however, if fat accounts for more than 10% of your liver's weight, a subject is considered to have fatty liver and is at a risk for developing more serious complications.

Fatty liver may cause no damage, but sometimes the excess fat leads to inflammation of the liver, which results in liver damage. This condition, called steatohepatitis, does cause liver damage. Sometimes, inflammation from a fatty liver is linked to alcohol abuse; this is known as alcoholic steatohepatitis. Otherwise the condition is called nonalcoholic steatohepatitis, or NASH. A fatty liver produces no symptoms on its own, and people often learn about their fatty liver when they have medical tests for other reasons. NASH can damage the liver for years or even decades without causing any symptoms.

Eating excess fat and/or calories causes fat to build up in the liver. When the liver does not process and break down fat as it normally should, too much fat will accumulate. People tend to develop fatty liver if they have certain other conditions, such as obesity, diabetes, or high triglycerides. Alcohol abuse, rapid weight loss and malnutrition may also lead to fatty liver. However, some people develop fatty liver even if they have none of these conditions. More information on fatty liver disease is available publicly on the world wide web at liverfoundation.org/education/info/fattyliver/.

Alzheimer's Disease

Alzheimer's disease (AD) is the most common form of dementia among older people. AD begins slowly. It first involves the parts of the brain that control thought, memory and language. AD usually begins after age 60. The risk goes up as you get older. Your risk is also higher if a family member has had the disease. Currently, no treatment can stop the disease.

A hallmark of all forms of Alzheimer's disease (AD) is an abnormal accumulation of the -amyloid protein (A) in specific brain regions. Both the generation and clearance of A are regulated by cholesterol. Elevated cholesterol levels increase A in cellular and most animal models of AD, and drugs that inhibit cholesterol synthesis lower A in these models. The identification of a variant of the apolipoprotein E (APOE) gene as a major genetic risk factor for AD is also consistent with a role for cholesterol in the pathogenesis of AD. Thus, lowering neuronal cholesterol levels is a strategy for treating and preventing AD. A review by Simons et al. (Neurology 2001. 2001 September 25; 57(6):1089-93.) discusses a link between cholesterol and AD, and discusses how cholesterol might modulate Abeta deposit formation.

Diabetes

People with diabetes are more likely to suffer from, and die from, cardiovascular problems (like a heart attack or stroke) than those without diabetes. Diabetes can upset the balance between HDL and LDL levels. People with diabetes tend to have LDL particles that stick to arteries and damage their walls more easily. Glucose latches onto lipoproteins, and these glucose coated LDL particles remain in the bloodstream longer and may lead to plaques. People with diabetes tend to have low HDL and high triglyceride levels, both of which boost the risk of heart and artery disease. As a result, in people with diabetes: heart disease occurs earlier, heart disease is two to four times as common, and heart disease is more often fatal. Accordingly, heart disease in people with diabetes is a major public health problem, one that is expected to get worse. A Centers for Disease Control and Prevention study estimated that one-third of babies born in 2000 will someday develop diabetes. People can reduce their risk of heart and blood vessel disease by lowering their cholesterol levels.

Metabolic Syndrome

Metabolic syndrome is a disease or disorder wherein the patient has high LDL cholesterol, low HDL cholesterol and high triglyceride levels in blood. People with metabolic syndrome are at increased risk of coronary heart disease and other diseases related to plaque buildups in artery walls (e.g., stroke and peripheral vascular disease) and type 2 diabetes. The metabolic syndrome has become increasingly common in the United States, and it is estimated that over 50 million Americans have it.

Metabolic syndrome can be characterized by a group of metabolic risk factors that include: abdominal obesity (excessive fat tissue in and around the abdomen); atherogenic dyslipidemia (blood fat disorders—high triglycerides, low HDL cholesterol and high LDL cholesterol—that foster plaque buildups in artery walls); Elevated blood pressure; Insulin resistance or glucose intolerance (the body can't properly use insulin or blood sugar); Prothrombotic state (e.g., high fibrinogen or plasminogen activator inhibitor-1 in the blood); Proinflammatory state (e.g., elevated C-reactive protein in the blood).

Lowering LDL cholesterol to recommended levels is among the first lines of therapeutic aims in treating the metabolic syndrome.

Hypo-Alphaproteinemia

Hypo-alphaproteinemia is a disease where the patient has the inability to synthesize sufficient amount of HDL and or catabolizes HDL rapidly.

II. Eu Mil

EuMil is a polyherbal formulation consisting of equal portions of standardized extracts of *Embilica officinalis Gaertn* (syn. *Phyllanthus embilica* Linn.) (EO), *Withania somnifera* (L) Dunal and *Ocimum sanctum* L with *Asparagus racemosus Willd* used as filler [9-11]. Although EuMil is usually prescribed as an anti-stress and performance enhancing herbal medicine, little is known about its hypocholesterolemic properties. For instance, in a study by Bhattacharya et al. (Indian J Exp Biol. 2002 October; 40(10):1161-3) examined anti-stress activity of EuMil, but provided no teaching or suggestion of any anti-cholesteremic activity. Here, applicants have shown that EuMil has hypocholesterolemic properties in a formulation fed to rabbits with experimental hyperlipidemia, (U.S. Provisional Application 60/876,761 filed Dec. 22, 2006, U.S. Provisional Application 60/877,753 filed Dec. 29, 2006, U.S. Provisional Application 60/876,599 filed Dec. 22, 2006 and U.S. Provisional Application 60/877,740 filed Dec. 29, 2006, all incorporated by reference herein). Further research has shown that the only component of EuMil that had significant hypocholesterolemic activity was the powdered fruit of EO.

The fruit of EO (Amla in Hindi) is widely used in India, Sri Lanka, Pakistan, Uzbekistan, South East Asia and China as a traditional medicine to treat many diseases such as diarrhea, jaundice, dyspepsia and hemorrhage amongst others [12-14]. The activity of Amla usually has been ascribed to its high content of vitamin C, which is stabilized in the fruit due to presence of tannins [15, 16].

Previous Ayurvedic studies have suggested that several herbal mixtures exert their effect in a synergistic manner. Moreover, since EuMil is made up of a admixture of EO, *W. somnifera* and *O. sanctum* (with *Asparagus racemosus* used as a filler for pill preparation), the instant invention is focused on whether this herbal preparation exerted its hypocholesterolemic effect in a synergistic or additive manner (e.g. as a mixture) or whether the activity was confined to only one of the above herbal ingredients.

III. Compounds

As described herein, EuMil is made up of a mixture of EO, *W. somnifera* and *O. sanctum* (with *Asparagus racemosus* used as a filler for pill preparation).

The invention features in certain embodiments isolated fractions of EuMil as set forth below, and numbered as compounds (1), (2a), (2b), (3,) (4), (5), (6), (7), (8), (9), (10), (11), (12) and (13).

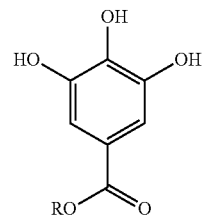

R = H gallic acid (1)
R = CH₃ methyl gallate (2a)
R = CH₂CH₃ ethyl gallate (2b)

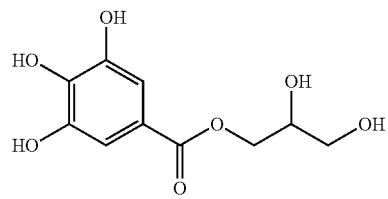

glycerol-1-gallate (3)

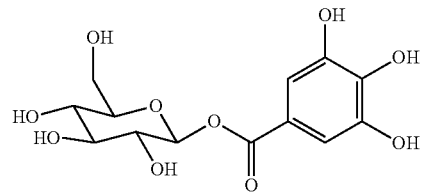

GG1 (4)

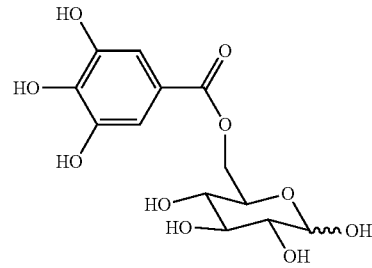

GG6 (5)

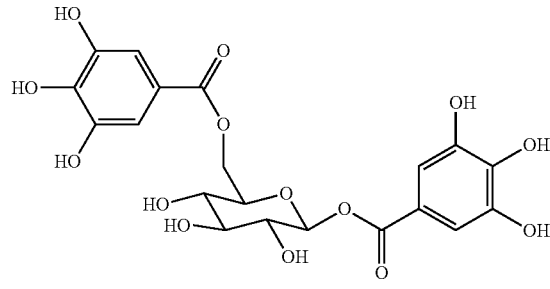

DGG16 (6)

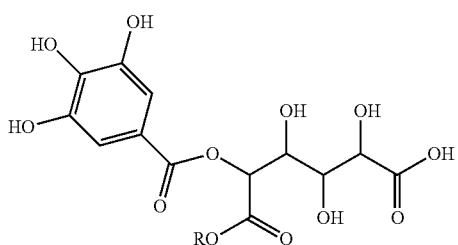

R = H mucic acid 2-gallate (7)
R = CH₃ mucic acid 1-methyl ester 2-gallate (8)

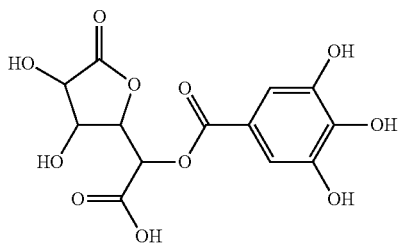

mucic acid 1,4-lactone 5-gallate (9)

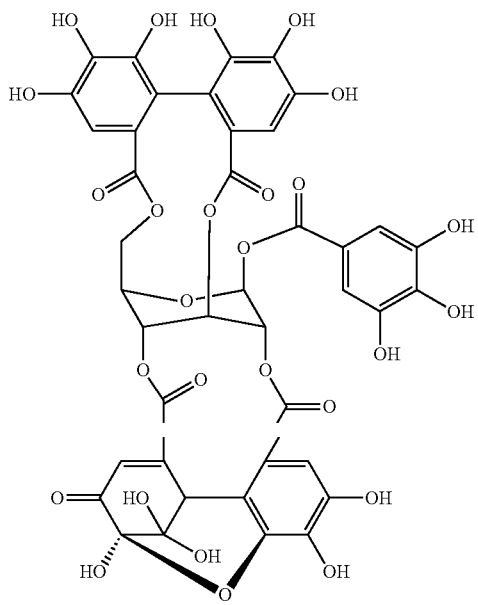

geraniin (10)

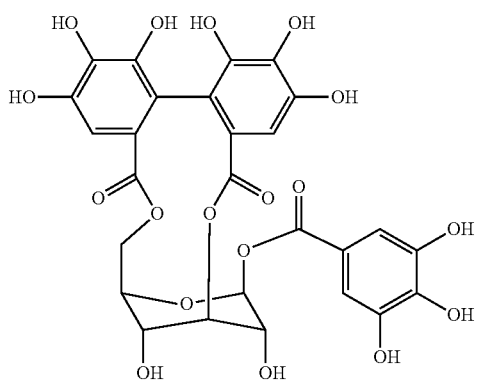

corilagin (11)

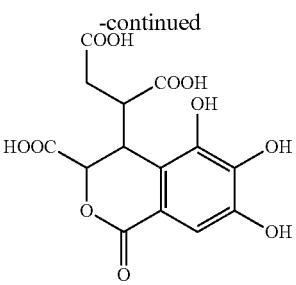

chebulic acid (12)

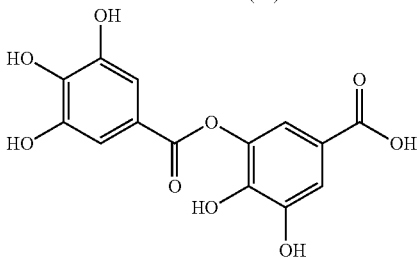

m-digallic acid along with minor
amounts of p-digallic acid (13)

In certain embodiments, the invention features administering to a subject an effective amount of one or more gallic acid derivatives. In more specific examples, the gallic acid derivatives are selected from the compounds as described above, compounds 2 (a) and (b)-13.

In other certain embodiments, the compound used is compound 4.

In other certain embodiments, the compound used is compound 5.

In other certain embodiments, the compound used is compound 7.

In other certain embodiments, the compound used is compound 8.

In other certain embodiments, the compound used is compound 9.

In certain preferred embodiments, the first compound of choice will be compound 4, the second most preferred will be compound 5, the third most preferred will be compound 7, the third most preferred will be compound 8, the fourth most preferred will be compound 9.

In certain embodiments, the one or more gallic acid derivatives are combined, for example combinations of two, three or more gallic acid derivatives. The gallic acid derivatives may be combined as one or more of a cholesterol lowering gallate derivative with one or more of a cholesterol uptake/absorption inhibitor.

In certain preferred embodiments, the gallic acid derivatives are combined as, but not limited to the following combinations:

Compound 4+Compound 5+Compound 2a
Compound 4+Compound 8+Compound 2a
Compound 4+Compound 5+Compound 7
Compound 4+Compound 2a
Compound 4+Compound 2b
Compound 7+Compound 2b
Compound 5+Compound 8
Compound 5+Compound 7

Gallic acid (Compound 1) has been shown to have to toxic effects. For example, in a 2001 report (Food and Chemical Toxicology Volume 39, Issue 11, November 2001, Pages 1063-1070), Shibutani et al. reported the toxicity of gallic acid (GA) was investigated in F344 rats by feeding a diet containing 0, 0.2, 0.6, 1.7 and 5% GA for 13 weeks. Toxicological parameters included clinical signs, body weight, food consumption, hematology, blood biochemistry, organ weights and histopathological assessment. Body weight gain in the 5% GA-treated animals of both sexes from week 1 to the end of the experiment was significantly lower than that of the untreated controls. Toxic effects following administration of 0.6% or more in males and 5% in females included reduction of hemoglobin concentration, hematocrit and red blood cell counts and increase in reticulocytes. Histopathologically, extramedullary hematopoiesis, hemosiderin deposition and congestion appeared in the spleens of 5% GA-treated animals, suggesting development of hemolytic anemia. In addition, centrilobular liver cell hypertrophy, reflected in increase in liver weight, was observed in animals of both sexes.

Gallic acid has been shown to have apoptotic effects. For example, reports by Qui X. et al (Heart and Vessels 15: 90-99 (2000)), Inoue, M (BBRC 204: 898-904, (1994)), Serrano A et al. (Archiv. Biochem. Biophys. 350: 49-54 (1995)), Hsu, C L et al. (J. Agric. Food. Chem. 55: 354-7356 (2007)) show that apoptosis is a mechanism of action of gallic acid.

IV. Methods of Treatment

The invention provides various methods of using the compounds of the invention for disease therapy. Generally, the compounds of the invention as described herein are useful to treat an elevated blood lipid level-related disease or disorder (e.g. hypercholesteremia) as well as for providing a delivery vehicle for therapeutic agents (including, but not limited to, cholesterol-lowering agents, triglyceride-lowering agents and other lipid-lowering agents).

In one aspect, the invention features methods for preventing or treating an elevated blood lipid level-related disease or disorder in a subject comprising administering to the subject an effective amount of one or more gallic acid derivatives, and thereby preventing or treating an elevated blood lipid level-related disease or disorder in the subject. Blood lipid level related diseases and disorders, as discussed in more detail herein, can be selected from, but not limited to hyperlipidemia, arteriosclerosis, fatty liver, angina pectoris, stroke, alzheimer's disease, obesity, diabetes, arthritis, and inflammatory diseases.

The invention also features methods for preventing or treating inflammation or a stress response in a subject comprising administering to the subject an effective amount of one or more gallic acid derivatives, thereby preventing or treating inflammation in the subject.

Inflammation is associated with a large collection of mediators that initiate the inflammatory response, recruit and activate other cells to the site of inflammation, and subsequently resolve the inflammation (Gallin and Snyderman, 1999, Overview in INFLAMMATION: BASIC PRINCIPLES AND CLINICAL CORRELATES, 3 d ed., Lippincott Williams & Wilkins, Philadelphia, pp. 1 3). Hypercholesterolemia has been associated with high plasma levels of inflammation-sensitive plasma proteins (ISP). In a study done by Engstrom et al. (Circulation. 2002; 105:2632-2637), Plasma cholesterol and 5 inflammation-sensitive plasma proteins (ISP) (fibrinogen, alpha 1-antitrypsin, haptoglobin, ceruloplasmin, and orosomucoid) were determined in 6063 healthy men, 28 to 61 years of age. The incidence of stroke, cardiac events (fatal and nonfatal), and cardiovascular deaths was compared between groups defined by levels of cholesterol and ISP. High cholesterol was associated with higher levels of ISP. Hypercholesterolemia (6.5 mmol/L, 251 mg/dL) was associated with an increased incidence of ischemic stroke and cardiac events and with a reduced incidence of intracerebral hemorrhage. The ISP levels modified these associations. After risk factor adjustment, men with hypercholesterolemia and high ISP levels had a significantly higher risk of cardiovascular death, cardiac events, and ischemic stroke than men with normal cholesterol and low ISP levels. In the absence of high ISP levels, hypercholesterolemia was associated with a moderately higher risk of cardiovascular death and cardiac events, but not significantly with ischemic stroke.

Elevated stress has been associated with lipid-level related disorders. Macrophages are the most prominent cell type in atherosclerotic lesions. They are present throughout the process of lesion development and characteristically accumulate 'free' cholesterol—an unesterified form of cholesterol. This accumulates in endoplasmic reticular (ER) membranes, which are normally devoid of cholesterol. Such abnormal accumulation of 'free' cholesterol has several adverse effects on ER function, and ultimately results in a stress response.

Additionally, work by Werstuck et al. (J Clin Invest, May 2001, Volume 107, Number 10, 1263-1273) has shown that homocysteine-induced endoplasmic reticulum (ER) stress activates both the unfolded protein response and the sterol regulatory element-binding proteins (SREBPs) in cultured human hepatocytes as well as vascular endothelial and aortic smooth muscle cells, and that activation of the SREBPs is associated with increased expression of genes responsible for cholesterol/triglyceride biosynthesis and uptake and with intracellular accumulation of cholesterol.

As discussed in more detail herein the one or more gallic acid derivatives is, in certain preferred embodiments, administered as a nutraceutical.

As discussed in more detail herein the one or more gallic acid derivatives are, in other certain preferred embodiments, selected from the group consisting of: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

As described herein, the one or more gallic acid derivatives can be a combination of compounds. In certain embodiments, the gallic acid derivatives may be combined as one or more of a cholesterol lowering gallate derivative combined with one or more of a cholesterol uptake/absorption inhibitor. Accordingly, in certain examples, the one or more gallic acid derivatives are selected from, but not limited to, combinations of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

The invention also features methods of affecting (reducing or increasing) cholesterol metabolism. By cholesterol metabolism is meant cholesterol biosynthesis, cholesterol cellular efflux and/or cholesterol cellular uptake. In particular, the invention features methods of reducing cholesterol biosynthesis in a subject comprising administering an effective amount of one or more gallic acid derivatives, thereby reducing cholesterol biosynthesis in a subject.

The invention features methods of increasing the cellular efflux of cholesterol in a subject comprising administering an effective amount of one or more gallic acid derivatives, thereby increasing the cellular efflux of cholesterol in a subject.

The invention features methods of inhibiting the cellular uptake of cholesterol in a subject comprising administering an effective amount of one or more gallic acid derivatives, thereby inhibiting the cellular uptake of cholesterol in a subject.

The invention also features methods of inhibiting the oxidation of LDL comprising administering an effective amount of one or more gallic acid derivatives, thereby preventing the oxidation of LDL.

As discussed in more detail herein the one or more gallic acid derivatives is, in certain preferred embodiments, administered as a nutraceutical.

As discussed in more detail herein the one or more gallic acid derivatives are, in other certain preferred embodiments, selected from the group consisting of: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

As described herein the one or more gallic acid derivatives can be a combination of compounds. In certain embodiments, the gallic acid derivatives may be combined as one or more of a cholesterol lowering gallate derivatives combined with one or more of a cholesterol uptake/absorption inhibitor. Accordingly, in certain examples, the one or more gallic acid derivatives are selected from, but not limited to, combinations of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7. In any of the methods as described, one or more second agents can be administered along with the one or more gallic acid derivatives.

V. Compositions

As reported herein, one or more gallic acid derivatives has effects on cholesterol synthesis, cholesterol level and/or cholesterol metabolism (e.g. efflux, uptake). Accordingly, in certain examples, the invention features a pharmaceutical composition for the treatment or prevention of an elevated blood lipid level-related disease or disorder comprising one or more gallic acid derivatives and a pharmaceutically acceptable excipient.

The compositions should be sterile and contain a therapeutically effective amount of the polypeptides or nucleic acid molecules in a unit of weight or volume suitable for administration to a subject. A gallic acid derivative may be administered within pharmaceutically-acceptable diluents, carriers, or excipients, in unit dosage form. Conventional pharmaceutical practice may be employed to provide suitable formulations or compositions to administer the compounds to patients suffering from the disease or disorder to be treated, for example a disease or disorder of elevated lipid level. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

With respect to a subject having an elevated blood lipid level-related disease or disorder, an effective amount is sufficient to stabilize, slow, or reduce the progression or symptoms or presentation of the elevated blood lipid level-related disease or disorder. With respect to a subject having inflammation or a stress response, an effective amount is sufficient to stabilize, slow, reduce, or reverse the inflammation or the stress response.

Methods well known in the art for making formulations are found, for example, in "Remington: The Science and Practice of Pharmacy" Ed. A. R. Gennaro, Lippincourt Williams & Wilkins, Philadelphia, Pa., 2000.

The pharmaceutical compositions may comprise any form of gallic acid that is derived from EuMil. More specifically, the gallic acid derivative can be selected from the group comprising: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid.

The gallic acid derivatives can be selected from a combination of gallic acid derivatives selected from the group consisting of: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

The compositions of the invention can be administered in many dosage forms. In certain examples, the dosage form is selected from a food composition, tablet, pill, gel, capsule, a patch, a suspension tablet, liquid, solution, aqueous emulsion powder, lozenge, sachet, cachet, elixir, suspension, emulsion, solution, syrup, aerosol, ointment, soft gelatin capsule, and hard gelatin capsule, suppository, creams, lotions, solutions, gels, pastes powder, and suspension. The food can be a health food product, a food product made from cereal flour, gums, a dairy product, a soup, a broth, a paste, a sauce, a beverage, a vitamin complex, a food rich in cholesterol, salt, or pepper.

In certain preferred examples, the compositions of the invention can be administered in a patch form. For example, the compounds can be adsorbed to patches which can be affixed to the skin. For example, the patches can have use in patients with Xanthalasma, a disorder characterized by orange crystals of cholesteryl ester deposits in the eyelids.

Combination Treatments

The invention further contemplates combination therapies. In the present invention, the one or more gallic acid derivatives can be administered either alone or in combination with other agents known to affect, e.g. lipid levels, where combining compounds or extracts would lead to synergistic effects.

In one embodiment, a composition comprising the compounds of the invention as described herein will further comprise a therapeutic agent.

In certain examples, the therapeutic agent is selected from the group consisting of, but not limited to, inhibitors of cholesterol metabolism, inhibitors of triglyceride synthesis, beta blockers, diuretics, inhibitors of platelet aggregation, angiogenesis inhibitors angiogenesis inhibitors, arthritis medication, toxins, anti-inflammatory agents. The toxins may be, for example botulinum toxin.

The therapeutic agent may be a small molecule or macromolecule such as peptide, protein or nucleic acid. The therapeutic agent may be selected from the group consisting of bile-acid-binding resins, which interrupt the recycling of bile acids from the intestine to the liver (including cholestyramine (QUESTRAN LIGHT, Bristol-Myers Squibb), and colestipol hydrochloride (COLESTID, Pharmacia & Upjohn Company)); statins, which inhibit cholesterol synthesis by blocking HMG-CoA—the key enzyme involved in cholesterol biosynthesis (including lovastatin (MEVACOR, Merck & Co., Inc.), a natural product derived from a strain of *Aspergillus*, pravastatin (PRAVACHOL, Bristol-Myers Squibb Co.), and atorvastatin (LIPITOR, Warner Lambert)) cerivastatin (BAYCOR (Bayer)), fluvastatin (LESCOL (Sandoz)), and simvastatin (ZOCOR (Merck)); niacin, a water-soluble vitamin B-complex which diminishes production of VLDL and is effective at lowering LDL; fibrates, lower serum triglycerides by reducing the VLDL fraction and may in some patient populations give rise to modest reductions of plasma cholesterol via the same mechanism (including clofibrate (ATROMID-S, Wyeth-Ayerst Laboratories), and gemfibrozil (LOPID, Parke-Davis)]; estrogen replacement therapy, lowers cholesterol levels in post-menopausal women; long chain alpha, omego-dicarboxylic acids have been reported to lower serum triglyceride and cholesterol (See, e.g., Bisgaier et al., 1998, J. Lipid Res. 39:17-30; WO 98/30530; U.S. Pat. No. 4,689,344; WO 99/00116; U.S. Pat. Nos. 5,756,344; 3,773, 946; 4,689,344; 4,689,344; 4,689,344; and 3,930,024); other compounds including ethers (See, e.g., U.S. Pat. Nos. 4,711, 896; 5,756,544; 6,506,799), phosphates of dolichol (U.S. Pat. No. 4,613,593), and azolidinedione derivatives (U.S. Pat. No. 4,287,200) are disclosed as lowering serum triglyceride and cholesterol levels.

Preferably, the therapeutic agent is attached to the gallic acid derivative by a covalent linkage. Any covalent linkage is appropriate for attachment of the gallic acid derivative and the therapeutic agent.

The therapeutic agent can be administered in combination with the one or more gallic acid derivatives.

In certain embodiments, the compounds of the invention can be administered with other agents to achieve a therapeutic effect, e.g. can be administered with other therapeutics to treat an elevated blood lipid level-related disease.

In some embodiments, the amount of compound, e.g. any one of the compounds 2a-13 as described herein, that is required to achieve a therapeutic effect, when co-administered with another agent that has an effect to treat an elevated blood lipid level-related disease, is less than about 85% of the amount of compound (e.g. compound 2a-13 or combinations thereof) required to achieve the therapeutically effect when administered in the absence of the other therapeutic (e.g., less than about 80%, less than about 75%, less than about 70%, less than about 65%, less than about 60%, less than about 55%, or less than about 50%). In certain examples, the invention contemplates the administration of other therapeutic agents which possess the capacity to reduce the level of cholesterol and/or LDL and/or triglycerides and/or other lipids in the blood of a mammal, and are considered useful in a composition in combination with compounds of the present invention.

In one embodiment, one or more of the compounds of the instant invention and one or more agents, e.g. a therapeutic agent, are administered simultaneously in a combined amount effective to produce the desired therapeutic outcome. This is achieved by administering a single composition or pharmacological formulation that includes all of the active agents, or by administering to the subject two distinct compositions or formulations, at the same time, wherein one composition includes one or more of the compounds of the instant invention, and the second composition includes the therapeutic agent. The one or more of the compounds of the instant invention and other therapeutic agent(s) may or may not exhibit the same mechanism by which they reduce the levels of total cholesterol (i.e., hypercholesteremia) and/or other lipids in a mammal.

Alternatively, treatment with the one or more of the compounds of the instant invention may precede or follow therapy with another therapeutic agent by intervals ranging from minutes to weeks. In embodiments where two or more therapeutic compositions are administered separately, one would generally ensure that a significant period of time did not expire between the time of each delivery, such that the second therapeutic agent and one or more of the compounds of the instant invention would still be able to exert an advantageously combined effect. In such instances, it is contemplated that one would administer one or more compositions within about 12-24 hours of each other, or about 6-12 hours of each other, or with a delay time of only about 12 hours. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Exemplary therapeutic agents that can be used in combination therapy include, but are not limited to, the following:

Statin-Related Agents

In one embodiment, the therapeutic agent in the combination therapy is a statin-related agent. The term "statin-related" refers to any statin drug that is presently on the market, or is modified from the presently marketed statin drugs, and has a therapeutic effect when combined with the compositions described herein. As such it should be understood that analogs and variants of preexisting statins are contemplated to be useful herein. Such analogs or variants may be produced through rational drug design techniques known to those of skill in the art. In particular, statin drugs are known as HMG-CoA reductase inhibitors. These drugs are presently in clinical use as drugs in the battle against high cholesterol and in the control of heart attacks, both recurrent and first heart attacks. These agents generally have few side effects, and help not only to lower overall cholesterol, LDL cholesterol and triglycerides, but also to increase HDL cholesterol. The use of other compounds in the combination therapy that interfere with the activity of HMG-CoA reductase is considered as an aspect of the invention.

Statins are exemplified by lovastatin (CAS Registry No. 75330-75-5; also known as mevinolin or monacolin K), and analogs of this compound have been described in numerous publications and patents. Exemplary statin compositions that are commercially available include LIPITOR (atorvastatin), PRAVACHOL (pravastatin), ZOCOR (simvastatin), MEVACOR (lovastatin), and LESCOL (fluvastatin). Methods of preparing such compounds are well known to those of skill in the art (see e.g., U.S. Pat. Nos. 6,521,762; 4,420,491; 4,342, 767; 4,319,039; 4,294,846; 4,444,784; 4,582,915 and 4,820, 850, all of which are incorporated by reference in their entireties herein). As described in the foregoing patents, statins are traditionally produced through fermentation using organisms from the *Aspergillus* genus, *Monascus* genus, *Pleurotus* genus, *Coniothyrium* genus and the like (see U.S. Pat. No. 6,521,762, incorporated by reference herein for review of fermentation procedures).

Moreover, formulations of statins as pharmaceutical medicament have been described in e.g., the Physician's Desk Reference. For example, tablet formulations of LIPITOR (atorvastatin calcium) are described at pages 2547-2551 (Parke-Davis, NJ.) and 2610-2613 (Pfizer, NY) of the Physician's Desk Reference (57.sup.th Edition, 2003). These formulations are supplied as tablets of atorvastatin calcium containing 10 mg, 20 mg, 40 mg, 50 mg, and 80 mg atorvastatin. The tablets are administered in doses ranging from 10 mg/day to 80 mg/day. The compositions of LIPIOR presently being used to lower cholesterol in humans may be used in the combined treatments of the present invention to produce a therapeutic amelioration of elevated lipid related diseases or disorders.

PRAVACHOL (pravastatin sodium; Bristol-Myers Squibb, NY), is another exemplary commercially available statin that may be used in the combined therapies of the present invention. PRAVACHOL is supplied as a 10 mg, 20 mg, 40 mg, and 80 mg tablets. These tablets may be administered at a daily dose of ranging from 10 mg/day to 80 mg/day. In exemplary treatments for hypercholesterolemia, 40 mg/day are administered as a single daily dose, with or without food. However, it is generally appreciated that this dose may be increased or lowered depending on the level of renal and liver function of the patient being treated. The administration doses and treatment guidelines for PRAVACHOL are discussed in further detail at pages 1101-1105 of the Physician's Desk Reference (57.sup.th Edition, 2003) and may be used to provide guidance for the use of statins in the methods of the present invention.

ZOCOR (simvastatin; Merck & Co., Inc., NJ), is another exemplary statin composition that may be used in combination with the layered phyllosilicate material of the present invention. Formulations of simvastatin are described at pages 2126-2131 of the Physician's Desk Reference (57.sup.th Edition, 2003). The daily doses may range from 5 mg/day to 80 mg/day and those of skill in the art are referred to the Physician's Desk Reference for further guidance regarding treatment protocols that may be used and/or modified for the present invention.

MEVACOR (lovastatin; Merck & Co., Inc. NY), and LESCOL (fluvastatin) are other exemplary statins that are described in the Physician's Desk Reference (57th Edition, 2003) at pages 2036-2041 and 2283-2287, respectively. Those of skill in the art will readily be able to modify the above-referenced pharmaceutical compositions that comprise various statin-related agents for the methods of the present invention.

For treatment protocols, those of skill may use the guidelines used for the any of the above-referenced pharmaceutical statins. Administration of ordinary tablets containing statin once, twice, three or more times a day. Accordingly, the skilled artisan may use dosages that have previously proven effective for the above indications as a preliminary measure of the amount of any of the above-referenced statins, to use in the therapeutic methods of the invention. Oral doses of the statins are particularly contemplated. Such oral doses may comprise the administration of between about 5 mg to about 80 mg statin drug on a daily basis. However, larger doses e.g., up to 200 mg/day also may be used. It should be understood the subject may receive more or less of the statin or other cholesterol lowering agent. Also it should be understood that similar doses may be administered through other routine routes of administration. The statin or other cholesterol lowering agent may be delivered in a single dose or alternatively may be subdivided and administered in multiple doses over a given period of time.

Nicotinic Acid

In another embodiment, the therapeutic agent in the combination therapy is nicotinic acid. Nicotinic acid (niacin) lowers total and LDL cholesterol and raises HDL cholesterol, and also lowers triglycerides. The dose of niacin required to lower cholesterol is about 100 times more than the Recommended Daily Allowance (RDA) for niacin and thus can potentially be toxic. Therefore, the drug must be taken under a doctor's care.

Fibrates

In yet another embodiment, the therapeutic agent in the combination therapy is a fibrate. Fibric acid derivatives (fibrates) are a class of medications that lower blood triglyceride levels. Fibrates lower blood triglyceride levels by reducing the liver's production of VLDL and by speeding up the removal of triglycerides from the blood. Fibrates are also modestly effective in increasing blood HDL cholesterol levels; however, fibrates are not effective in lowering LDL cholesterol. Exemplary fibrates include, but are not limited to, Bezafibrate (e.g. BEZALIP), Ciprofibrate (e.g. MODALIM), Clofibrate, Gemfibrozil (e.g. LOPID) and Fenofibrate (e.g. TRICOR).

Bile Acid Resins

In still another embodiment, the therapeutic agent in the combination therapy is a bile acid resin. Bile acid resins, also known as bile acid sequesterants, are mainly used to treat patients with moderately elevated LDL-cholesterol and when cholesterol-lowering drug therapy is necessary in young adult men and premenopausal women. They are also sometimes combined with other cholesterol-lowering drugs like "statins" to decrease very high levels of cholesterol. Exemplary bile acid resins include, but are not limited to, Cholestyramine, Colestipol (Colestid), and Cholsevelam (Welchol).

Cholesterol Absorption Inhibitors

In yet another embodiment, the therapeutic agent in the combination therapy is a cholesterol absorption inhibitor. Ezetimibe (ZETIA) is the only prescription drug currently in this class. This drug prevents dietary cholesterol from being absorbed from the small intestine and entering the blood, thus lowering blood cholesterol levels. Synergistic compositions comprising a cholesterol absorption inhibitor and the layered phyllosilicate material is particularly contemplated.

Salicylic Acid

Also contemplated as a therapeutic agent in the combination therapy is salicylic acid (aspirin). Aspirin has been shown to have a protective effect against heart attacks in patients with clogged blood vessels, and can also be used in a composition according to the present invention. The cholesterol-reducing mechanism is believed to be based on the acidic properties of aspirin, and as such the acid deconjugates the bile:cholesterol complex, reducing bioavailability.

Phytosterols

In another embodiment, the therapeutic agent in the combination therapy is a phytosterol. Phytosterols, also known as plant sterols or stanols, are lipids having chemical structures similar to cholesterol, which are present in all plants including but not limited to vegetables, fruits, and grains, particularly in nuts, seeds, and plant oils. Phytosterols inhibit intestinal cholesterol absorption, thereby lowering plasma total and low-density lipoprotein (LDL) cholesterol levels. Daily consumption of about one to two grams of phytosterols reduces the risk for cardiovascular disease by about 25 to about 28% without causing any adverse effects. Twice per day consumption of about 0.40 grams of phytosterols or about 0.65 grams of phytosterol esters has also been shown to lower total cholesterol levels and LDL cholesterol levels by up to 10%. An extract of the soy plant—sitosterol—is available in a product called TAKE CONTROL (Lipton). And an extract of pine needles—sitostanol—is available in a similar product called BENECHOL (McNeil). The use of policosanol, derived from waxes of various plants including, but not limited to, sugar cane and yams, is also contemplated.

Alginates and Pectins

In yet another embodiment, the therapeutic agent in the combination therapy is a polysaccharide including but not limited to, alginate, pectin, gellan gum, xanthan gum and zooglan. Alginates, pectins and modifications thereof are reported to interact with dietary cholesterol and affect its absorption and excretion (see U.S. Pat. Nos. 5,141,927; 5,597,810; 7,026,302, Japanese Patent No. 09235234, and Kimura et al., J. Ethnopharmacol, 54(1):47 54 (1996), the disclosures of which are incorporated herein by reference in their entireties).

Lecithin

In another embodiment, the therapeutic agent in the combination therapy is Lecithin (CAS#8002-43-5). Leithin is usually used as a synonym for phosphatidylcholine, a phospholipid which is the major component of a phosphatide fraction isolated from egg yolk or soy beans. Lecithin is commercially available in high purity as a food supplement and for medical uses. For example, Lecithin 19 Grain is sold over the counter and claims that it reduces cholesterol.

In yet another embodiment, the compounds of the invention can be utilized as delivery vehicles. In one variation, the compounds can be used to deliver nucleic acids or proteins, for example an antibody against cholesterol. In other embodiments, gene constructs for SREBP-1 (sterol regulatory element binding transcription factor 1) or LDL receptor may be used. In another variation, the compound or composition is a delivery vehicle for a therapeutic agent described herein. Binding of a therapeutic agent to a compound of the invention can improve its delivery and subsequent absorption through mucosal membranes, including the ocular, dermal, nasal and intestinal membranes. Drug release from the compound can be induced by pH, ionic strength changes, and/or in response to temperature, ionic current or ultrasound.

In other embodiments, the compounds of the invention are used in lieu of or in conjunction with other drug delivery vehicles known in the art in order to increase cell targeting membrane permeability and absorption. Exemplary drug delivery systems known in the art include, but are not limited to, those described in U.S. Pat. Nos. 6,838,528; 6,797,704; 6,730,334; 6,706,289; 6,482,439; 6,443,989; 6,383,478; 6,165,440; 5,780,044; 5,759,563; 5,565,215; and U.S. Patent Application Publication Nos. 2007/0059327; 2007/0053845; 2007/00036278; 2007/0031340; 2007/0026048; 2007/0003610; 2006/0193787; 2006/0188543; 2006/0149392; 2006/0105049; 2006/0057206; 2006/0034925; 2005/0266090; 2005/0260276; 2005/0249798; 2005/0249774; 2005/0220754; 2005/0209345; 2005/0058603; 2005/0152965; 2005/0089572; 2005/0058701, the disclosures of which are all incorporated herein by reference in their entireties.

In one embodiment, the mammal is human. In other embodiments, the mammal is an animal. Exemplary animals include, but are not limited to, farm animals such as horses, cows, sheep, pigs, alpacas, llamas, camels, birds, and goats; companion animals such as dogs and cats; exotic and/or zoo animals; laboratory animals including mice, rats, rabbits, guinea pigs and hamsters.

VI. Nutraceuticals

The compositions of the invention can be formulated as nutraceuticals.

In certain embodiments, gallic acid derivatives can be used alone. For example, a EuMil extract can be used alone.

In certain examples, a nutraceutical is any substance that is a food or a part of a food or something that is added to a food, and provides medical or health benefits, including the prevention and/or the treatment of a disease or disorder. Nutraceuticals are often natural products that are identified from botanicals, and purified or partially purified and then included in foods.

The nutraceutical can be administered as a food, a food composition, a tablet, pill, gel, capsule, suspension tablet, liquid, solution, aqueous emulsion powder, lozenge, sachet, cachet, elixir, suspension, emulsion, solution, syrup, aerosol, ointment, soft gelatin capsule, and hard gelatin capsule, suppository, creams, lotions, solutions, gels, pastes powder, and suspension. The compounds, in certain preferred embodiments, may be adsorbed to patches and adhered to the skin surface.

The food can be a health food product, a food product made from cereal flour, gums, a dairy product, a soup, a broth, a paste, a sauce, a beverage, a vitamin complex, a food rich in cholesterol, salt, or pepper.

Gallic acid derivatives of the present invention can be used as a beverage. For example, the beverage can be a beverage that contains water, a sweetener and a suitable additive.

The nutraceuticals can be made as a dietary supplement. For dietary supplements, the extract can be added and mixed according to methods routine in the art. Dietary supplements for animals can be prepared in a variety of forms including, but not limited to, liquid, powder, or solid pill forms. In the present invention, the one or more gallic acid derivatives can be administered either alone or in combination with other agents known to affect, e.g. lipid levels, where combining compounds or extracts would lead to synergistic effects or additive effects.

Nutraceutical compositions can be packaged in a number of ways.

The controlled release of a physiologically active agent into an individual's system from a sustained release dosage form is often a desirable alternative to repeated administrations (e.g., after a prescribed number of hours) of the agent from conventional dosage forms (i.e., one controlled release dosage may provide the full daily regimen of active agent). Sustained release formulations incorporating water soluble cellulose ethers in a hydrophilic solid core matrix have been developed for this purpose. Upon contact with an aqueous environment, such formulations hydrate to form a gel layer on the surface of the solid core matrix, which limits entry of water into the solid core, thereby establishing a diffusion-controlled sustained release of the active ingredient therein.

Alternative sustained release formulations are based on solid core matrixes that have been coated with materials that can form membranes exhibiting sustained release characteristics. Examples of such materials include hydroxypropyl methylcellulose, shellac, fats, and waxes. One preparation for the sustained release of a nutraceutical includes a solid matrix coated with a coating comprising methylcellulose. The solid matrix contains a polyphenol and a therapeutically effective amount of a nutraceutical. U.S. Pat. No. 7,115,283, incorporated by reference in its entirety herein, describes preparations and methods for the controlled release of nutraceuticals. In certain examples, a biodegradable matrix material can be used for the time dependent release of compounds e.g. used in drug eluting stents to reach small capillaries in the brain.

U.S. Pat. No. 6,723,358, incorporated by reference in its entirety herein, describes an edible matrix composition that has a chewable texture and that contains at least one encapsulated component. Encapsulation of food components is described in Encapsulation and Controlled Release of Food Ingredients, edited by S. J. Risch and G. A. Reineccius, ACS Symposium Series 590 (1995). U.S. Pat. No. 5,183,690 to Carr, et. al. describes a continuous extrusion process using starch-based material to encapsulate components. The resulting products are in the form of particulates, which have gelatinized starch as a continuous domain, in which discontinuous domains of biologically active core material is entrapped.

VII. Dosage and Administration

The compositions of the invention alone, or in combination with one or more therapeutic agents as described herein, is administered by any route that delivers an effective dosage to the desired site of action, with acceptable (preferably minimal) side-effects. Numerous routes of administration are known, including for example, oral, rectal, vaginal, transmucosal, buccal or intestinal administration; parenteral delivery, including intraperitoneal intramuscular, subcutaneous, intramedullary injections, as well as intrathecal, cutaneous or intradermal injections; respiratory or inhalation, nasal, pulmonary and topical application, including ocular and transdermal applications.

When used in the above or other treatments, a "therapeutically effective amount" or an "effective amount" of a compound or a composition comprising a compound of the invention means a sufficient amount of one or more of the compounds of the invention is provided to treat disorders, at a reasonable benefit/risk ratio applicable to any medical treatment. It will be understood, however, that the total daily usage of the one or more compounds will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of compositions of the invention administered to a mammalian subject range from about 10 to about 500 mg/kg/day. In preferred embodiments, when a single compound is administered, the dose given is preferably in the range of 40 to 200 mg/kg/day. If desired, the effective daily dose may be divided into multiple doses for purposes of administration; consequently, single dose compositions may contain such amounts or submultiples thereof to make up the daily dose. The dosage regimen of a composition of the invention alone or in combination as described herein to be used in anti-cholesterol treatment will be determined by the attending physician considering various factors which modify the action of the administered composition, e.g., the patient's age, sex, and diet, the severity of any infection, time of administration and other clinical factors.

Multiple doses per day are contemplated to achieve appropriate systemic levels of the compositions of the present invention.

Since Applicants have shown that 40 mg daily intake of Simvastatin can lower blood levels of cholesterol, a range of 40 mg-200 mg per day of a single compound, for example in preferred embodiments compound 4, given alone, should be as effective as or better than simvastatin in lowering cholesterol, in increasing cellular efflux of cholesterol or inhibiting cellular uptake of cholesterol.

Likewise Vytorin (a mixture of 40 mg of Simvastatin+10 mg of ezetimibe) can lower blood cholesterol to 50%. In certain embodiments, different dosages of the compounds can be combined, for example one dosage level of a cholesterol lowering gallate derivative (e.g. compound 8) with another dosage level of a cholesterol uptake/absorption inhibitor (e.g. compound 3).

In preferred examples, the dosage comprises about 0.1% to about 95% gallic acid derivative weight to weight of the composition, for example 0.5%, 1%, 2%, 5%, 10%, 15%, 20%, 25%, 30%, 40%, 50%, 55%, 60%, 70%, 75%, 80%, 85%, 90%, 95% or more.

Oral dosage forms include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, supra). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material.

In addition to the compositions of the invention alone, or in combination as described herein, tablets prepared for oral administration will generally contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the material containing the compositions of the invention may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts (See, for e.g., Remington: The Science and Practice of Pharmacy, supra). Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Created as an alternate route of drug administration to improve patient compliance and reduce drug side effects, prescription skin patches are rapidly becoming an important healthcare product category. Advances in synthetic materials and patch design have led to patches that are more esthetically acceptable and that are capable of delivering sustained dosing of active compounds for several days in a smaller package.

Patches are advantageous for long term treatment. Long-term treatment is possible for those who require longer periods of treatment than are provided for by conventional treatment methods. For example, the present invention provides for a pre-determined period of treatment which may last as long as, for example, up to 1, 2, or more years after treatment begins.

The dosage form can be an immediate release, sustained release, and delayed release.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Although the present compositions may be administered orally, other modes of administration are contemplated as well. Exemplary modes of administration include transmucosal (e.g., U.S. Pat. Nos. 5,288,498; 6,248,760; 6,355,248; 6,548,490, the disclosures of which are incorporated herein by reference in their entireties), transurethral (e.g., e.g., U.S. Pat. Nos. 5,919,474 and 5,925,629, the disclosures of which are incorporated herein by reference in their entireties), vaginal or perivaginal (e.g., U.S. Pat. Nos. 4,211,679; 5,491,171 and 6,576,250, the disclosures of which are incorporated herein by reference in their entireties) and intranasal or inhalation (e.g., U.S. Pat. Nos. 4,800,878; 5,112,804; 5,179,079; 6,017,963; 6,391,318 and 6,815,424, the disclosures of which are incorporated herein by reference in their entireties). One of skill in the art would be able to modify a composition as described herein alone or in combination to be used in any of the modes of administration described herein.

The compositions of this invention can be employed in mixture with conventional excipients, i.e., pharmaceutically acceptable organic or inorganic carrier substances suitable for topical application which do not deleteriously react with the acid or the alcohol in the composition. The compositions of the invention can also include diluents, fillers, salts, buffers, stabilizers, solubilizers, and other materials well known in the art (Remington's Pharmaceutical Sciences 16th edition, Osol, A. Ed. (1980).

VIII. Kits

In related variations of the preceding embodiments, a composition comprising the compounds of the invention alone or in combination as described herein may be so arranged, e.g., in a kit or package or unit dose, to permit co-administration with one or more other therapeutic agents. In another aspect, the one or more gallic acid derivatives and the agent are in admixture. In some embodiments, the two components to the kit/unit dose are packaged with instructions for administering the two agents to a mammalian subject for treatment of one of the above-indicated disorders and diseases.

The kits can comprise any of the pharmaceutical compositions as described herein, and instructions for use.

In certain preferred examples, the invention features a kit for the use in preventing or treating an elevated blood lipid level-related disease in a mammal comprising one or more gallic acid derivatives.

In other examples, the invention features kits that can be used in preventing or treating inflammation or an elevated stress response.

In other examples, the invention features kits that can be use in reducing cholesterol biosynthesis, increasing the cellular efflux of cholesterol, or inhibiting the cellular uptake of cholesterol.

The one or more gallic acid derivatives can be selected from the group comprising: methyl gallate, ethyl gallate, glycerol-1-gallate, glucose-1-gallate (GG1), glucose-6-gallate (GG6), glucose-1,6-digallate (DGG16), mucic acid-2-gallate, 1-methyl mucate-2-gallate, mucic acid 1,4-lactone 5-gallate, geraniin, corilagin, chebilc acid, and m-digallic acid with minor p-digallic acid, and instructions for use.

Additionally, the gallic acid derivatives in the kits can be administered as a nutraceutical.

In certain embodiments, the kits comprise: Compound 4+Compound 5+Compound 2a, Compound 4+Compound 8+Compound 2a, Compound 4+Compound 5+Compound 7, Compound 4+Compound 2a, Compound 4+Compound 2b, Compound 7+Compound 2b, Compound 5+Compound 8, and Compound 5+Compound 7.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

Example 1

EuMil Mixture and Identification of Individual Components

Ayurvedic studies have suggested that several herbal mixtures exert their effect in a synergistic manner. Moreover, since EuMil is made up of a mixture of EO, *W. somnifera* and *O. sanctum* (with *Asparagus racemosus* used as a filler for pill preparation), the first study focused on whether this herbal preparation exerted its hypocholesterolemic effect in a synergistic manner or whether the activity was confined to only one of the above herbal ingredients.

The cell-based bioassays described herein revealed that only the EO component of EuMil significantly inhibited de novo biosynthesis of cholesterol. Bioassay-guided isolation from an EO aqueous alcoholic solution led to the isolation of purified gallic acid and mucic acid derivatives 1-9 as identified in Table 1, shown below. The structures of compounds 1-9 are shown in FIG. 1. These compounds are shown to have the hypocholesterolemic activity of the EO extract as demonstrated in the Examples described herein. In addition, compounds 10 through 13 of Table 1 were also isolated and their structures are shown in FIG. 1. Compounds 10-13 are also tested in the cell-based bioassay.

TABLE 1

| FIG. NO. | COMPOUND NAME | REFERENCE NO. |
|---|---|---|
| 1 | gallic acid | |
| 2a | methyl gallate | |
| 2b | ethyl gallate | |
| 3 | glycerol-1-gallate | 17-19 |
| 4 | glucose-1-gallate (GG1) | 20 |
| 5 | glucose-6-gallate (GG6) | 17, 19 |
| 6 | glucose-1,6-digallate (DGG16) | 17, 19, 21 |
| 7 | mucic acid-2-gallate | 20, 22 |
| 8 | 1-methyl mucate-2-gallate | 20.22 |
| 9 | mucic acid 1,4-lactone 5-gallate | 20, 22 |
| 10 | geraniin | |
| 11 | corilagin | |
| 12 | chebulic acid | |
| 13 | m-digallic acid along with minor p-digallic acid | |

The structure of each of these purified compounds isolated from the fruit of EO is shown in FIG. 1.

The structures of compounds 1 to 13 were determined by mass spectroscopy (MS) and nuclear magnetic resonance (NMR) spectroscopy, as well as comparison with previously reported data [17-22]. The $^1$H NMR spectrum of (GG6) (5) displayed resonances for both the α- and β-anomers, as was expected as all of these compounds have been previously isolated from EO except for glycerol-1-gallate (3) and GG6 (5).

Extraction and Polyamide Treatment of the Plant Components of EuMil

Plant powder from each component of EuMil was extracted with methanol. A portion of the methanol extract of each plant was eluted through Polyamide SC 6 (0.05-0.16 mm, Macherey-Nagel) to remove polymeric tannins and tested in the cell-based assays. Only the plant powder from EO was active, which indicated that most, if not all of the hypocholesterolemic properties of EuMil reside with the EO component of EuMil.

Crude EO powder (500 mg) was extracted with 25% ethanol in water (2×10 ml) and the extract dried by rotary evaporation to provide a crude extract (240 mg).

The crude extract was dissolved in water (4 ml), centrifuged and the supernatant separated using the preparative reversed-phase HPLC (see Fig. A1 see Appendix) (4 injections of 60 mg, YMC pack ODS-AQ column, RP18, 150×20 mm, 5 µM, isocratic in 100% H2O (with 0.1% HCOOH) for 30 minutes and linear gradient from 0% to 30% acetonitrile (with 0.1% HCOOH) for 40 minutes, flow rate 12 mL/min, UV detection 210 and 254 nm) to obtain mucic acid-2-gallate (7) (19.6 mg), mucic acid 1,4-lactone 5-gallate (9) (16.0 mg), 1-methyl mucate-2-gallate (8) (3.6 mg), a mixture of gallic acid (1) and glucose-1-gallate (GG1) (4) (9 mg mixture), glucose-6-gallate (GG6) (5) (1.2 mg), glucose-1,6-digallate (DGG16) (6) (5.2 mg) and glycerol-1-gallate (3) (2.4 mg) in order of elution (structures in FIG. 1). Methyl gallate (2a) and ethyl gallate (2b) were present in the extract when the percentage of methanol or ethanol respectively approached 50% and above and could be isolated using the same preparative HPLC conditions. Each of the compounds were characterized by (−)-HR-ESI MS and 1H, COSY, HSQC and HMBC NMR experiments and their spectroscopic data compared to previously reported data. The retention time of each compound was obtained using a YMC Pack-ODS-AQ column (S-5 mm, 150×4.6 mm, flow rate 1.0 mL/min) using isocratic 100% H2O (with 0.1% HCOOH) for 5 minutes and linear gradient from 0% to 30% acetonitrile (with 0.1% HCOOH) for 30 minutes.

The following purified compounds were identified and analyzed by the 25% ethanolic extraction:

Gallic acid (1): white powder; Rt 7.2 min; ESI-MS [M-H]− 169.0136; 1H NMR (D2O) d 7.14 (2H, s, galloyl). Identical to gallic acid purchased from Sigma Aldrich.

Methyl gallate (2a): white powder; Rt 14.9 min; ESIMS [M-H]− 183.0294; $^1$H NMR (D2O) d 3.83, (3H, s, OCH3), 7.14 (2H, s, galloyl).

Ethyl gallate (2b): white powder; Rt 19.0 min; ESIMS [M-H]− 197.0446; $^1$H NMR (DMSO-d6), δ 1.26 (t, J=7.6 Hz, OCH2CH3), 4.18 (q, J=7.6 Hz, OCH2CH3), 6.92 (2H, s, galloyl).

Glycerol-1-gallate (3): colourless oil, Rt. 13.2 min.; ESIMS [M-H]− 243.0457; 1H NMR (D2O) d 3.67, (1H, dd, J=12.0, 6.6 Hz, H-3), 3.73, (1H, dd, J=12.0, 4.7 Hz, H-3), 4.08 (1H, m, H-2), 4.34 (1H, dd, J=11.7, 6.0 Hz, H-1), 4.37 (1H, dd, J=11.7, 3.8 Hz, H-1), 7.19 (2H, s, galloyl).

Glucose-1-gallate (GG1) (4): white powder; Rt. 7.46 min; ESIMS (M-H)− 331.0665; 1H NMR (D2O) d 3.50 (1H, dd, J=9.4, 9.4 Hz, H-4), 3.65 (3H, m, H-2, H-3 and H-5), 3.75 (1H, dd, J=12.6, 5.6 Hz, H-6b), 3.91 (1H, dd, J=12.6, 2.2 Hz, H-6a), 5.74 (1H, d, 7.8 Hz, H-1), 7.23 (2H, s, galloyl).

Glucose-6-gallate (GG6) (5): white powder; Rt 16 4 min; ESIMS [M-H]-331.0678; 1H NMR (D2O) d 3.28-4.58 (H-2 to H-5 corresponding to the α and β isomers), 4.7 (1H, under residual solvent peak, H-1β), 5.23 (1H, d, J=4.1 Hz, H-1α), 7.18 (2H, s, galloyl).

Glucose-1,6-digallate (DGG16) (6): white powder; Rt 18.2 min, ESIMS [M-H]– 483.0778; 1H NMR (DMSO-d6) δ 3.30 (3H, m) and 3.59 (1H, m, H-2, H-3, H-4, H-5), 4.22 (1H, dd, J=12.0, 5.0 Hz, H-6b), 4.39 (1-H, dd, J=12.0, 1.9 Hz, H-6a), 5.55 (1H, d, J=8.2 Hz, H-1), 6.99 (2H, s, galloyl), 6.93 (2H, s, galloyl).

Mucic acid-2-gallate (7): colourless paste; Rt 2.7 min; ESIMS [M-H]-361.0402; 1H NMR (D2O) d 4.15 (1H, d, J=10.1, H-4), 4.39 (1H, dd, J=10.1, 1.3 Hz, H-3), 4.62 (1H, s, H-5), 5.51 (1H, d, J=1.3 Hz, H-2), 7.27 (2H, s, galloyl).

1-Methyl mucate-2-gallate (8): colourless paste; Rt 10.5 min; ESIMS [M-H]-375.0551; 1H NMR (D2O) d 3.84 (3H, s, OCH3), 4.12 (1H, dd, J=10.1, 1.6 Hz, H-4), 4.36 (1H, dd, J=10.1, 2.2 Hz, H-3), 4.47 (1H, d, J=1.9 Hz, H-5), 5.56 (1H, d, J=1.9 Hz, H-2), 7.28 (2H, s galloyl).

Mucic acid 1,4-lactone 5-gallate (9): colourless paste; Rt 4.9 min; ESIMS [M-H]– 343.0295; 1H NMR (D2O) d d4.41 (1H, dd, J=8.8, 8.7 Hz, H-3), 4.8 (1H, under residual solvent peak, H-2), 4.90 (1H, dd, J=8.5, 2 Hz, H-4), 5.48 (1H, s, H-5), 7.08 (2H, s galloyl).

1H, 13C and 2D NMR spectra were acquired on a BRUKER 500 MHz instrument using standard pulse sequences and parameters. NMR spectra were referenced to the residual protons in DMSO-d6 at δ 2.49 or in D2O with acetonitrile (δ 2.06) as an internal reference. Preparative HPLC was performed on a Gilson HPLC with a Gilson 322 pump, Gilson UV/VIS-156, with a Gilson 215 liquid handler using the UNIPOINT software. All of the compounds were analyzed by analytical HPLC using an Agilent 1100 HPLC system with a G1311A quaternary pump, G1313A ALS, G1315DAD, G1316A COLCOM and a G1322A degasser. High resolution electrospray mass spectral data were recorded on a Perspective Biosystems Mariner Biospectrometry TOF mass spectrometer.

Figure 2:
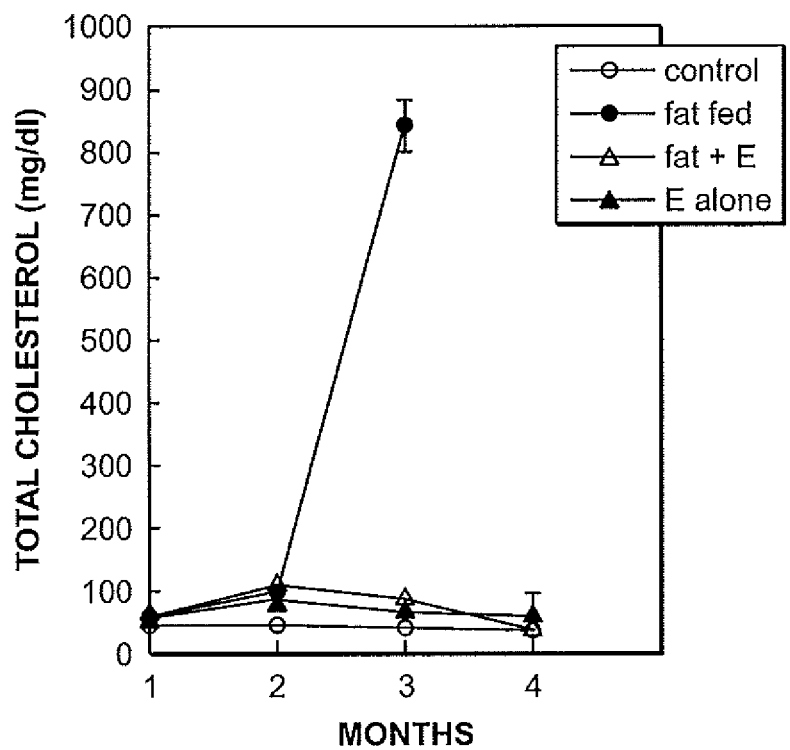
FIG. 2 is a graph that shows the effect of EuMil on the plasma level of cholesterol. Rabbits were fed a diet including rabbit chow (control), fat fed (14% coconut oil plus 0.2% cholesterol), fat fed plus EuMil (1 gm/kg), EuMil alone (1 gm/kg). At 1, 2, 3 and 4 month intervals blood was drawn and plasma levels of lipid/lipoprotein was measured. Values were derived from 3 rabbits in each group.

The HPLC chromatogram shown in FIG. 2 shows a complete profile of the compounds identified from a 3:1 ethanol:water extract of EO. The major compounds are mucic acid 2-gallate (7), followed by gallic acid (1) which co elutes with GG1 (4). Gallic acid (1) and GG1 (4) can be separated by additional HPLC separation. It should be noted that the mucic acid gallates derivatives 7 and 9 equilibrate in aqueous solutions as previously reported [22], while 1-methyl mucate-2-gallate (8) is not an artifact of the isolation procedure as it could be isolated when only ethanol, water and acetonitrile were used.

Example 2

Effect of EuMil on Cholesterol, LDL Cholesterol and Triglycerides in Rabbits

As shown in FIG. 2, rabbits fed a high fat and cholesterol diet for three months had markedly elevated level (17-fold higher as compared to control) of total plasma cholesterol (850 mg/dl). In contrast, the level of plasma cholesterol in control rabbits, fed EuMil (1 gm/kg of rabbit chow) and EuMil plus fat was similar up to four months.

Figure 3:
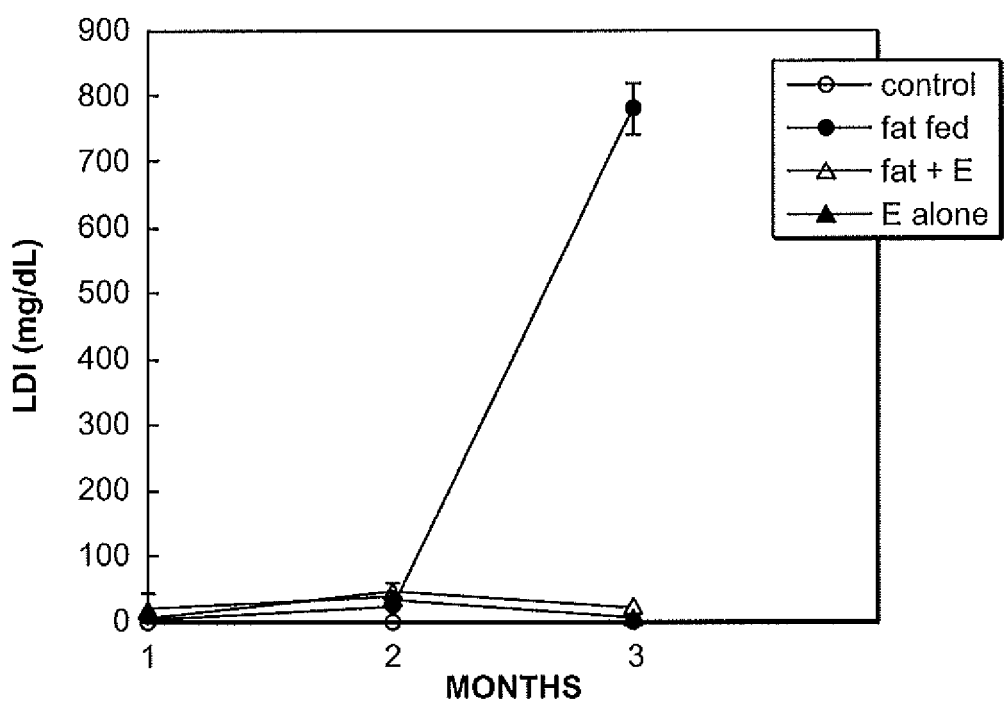
FIG. 3 is a graph that shows the effect of EuMil on the plasma LDL cholesterol levels in rabbits. Rabbits were fed rabbit chow (control), fat fed (14% coconut oil plus 0.2% cholesterol), fat fed plus EuMil (1 gm/kg), EuMil alone (1 gm/kg). Plasma samples were subjected to ultracentrifugation to isolate beta-lipoprotein particles (LDL/beta-VLDL). Values were derived from 3 rabbits in each group.

As expected, most of the increase in cholesterol in rabbits fed a high fat and cholesterol diet was associated with plasma low density lipoproteins (FIG. 3). In contrast, the plasma LDL cholesterol level in control rabbits, EuMil and EuMil plus fat fed rabbits were similar.

Figure 4:
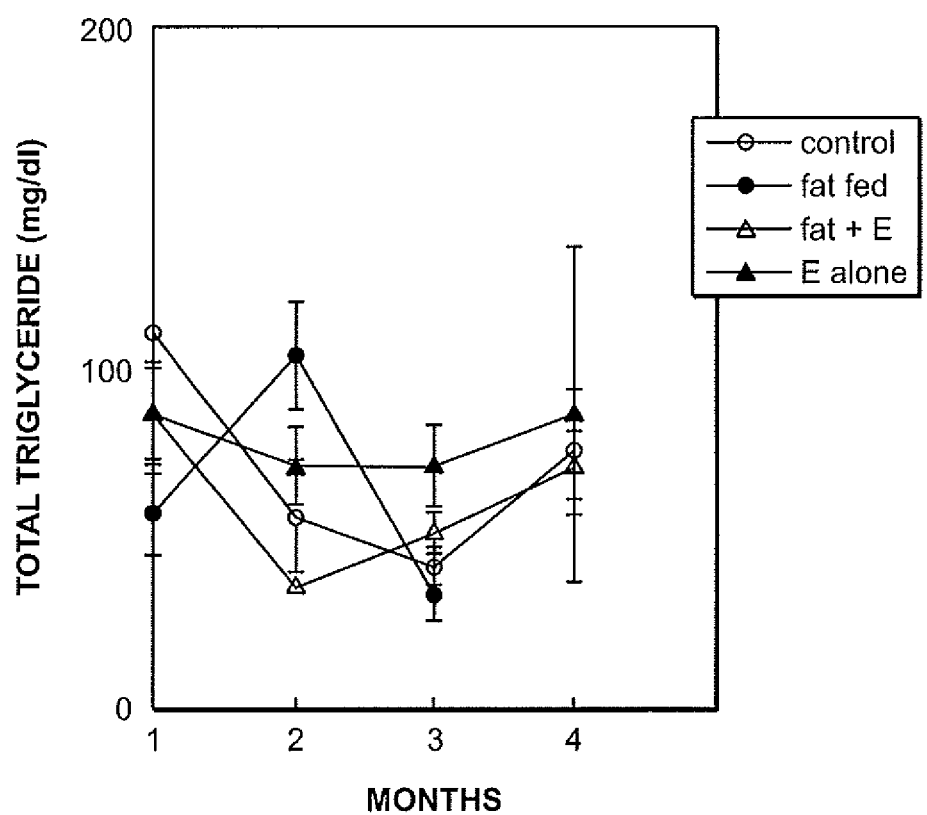
FIG. 4 is a graph that shows the effect of EuMil on the plasma triglyceride level in rabbits. Rabbits were fed rabbit chow (control), fat fed (14% coconut oil plus 0.2% cholesterol), fat fed plus EuMil (1 gm/kg), EuMil alone (1 gm/kg). The plasma samples were subjected to triglyceride assay. Values were derived from 3 rabbits in each group.

Following fat feeding for two-four months, the plasma level of triglycerides, shown in FIG. 4, was within the normal range. Feeding rabbits EuMil alone (throughout the four months of experimentation) did not alter the plasma level of triglycerides significantly as compared to control.

Example 3

Effect of EuMil on Cholesterol, LDL, Cholesterol Triglycerides and Apolipoprotein Levels in Human Subjects Next, experiments were carried out in human subjects to determine the effect of EuMil on cholesterol, LDL, cholesterol triglycerides and apolipoprotein levels. The studies conducted in human subjects (normal male and female), shown in FIG. 5, revealed the following. After 2 weeks of oral intake of EuMil (daily 500 mg) the levels of total cholesterol, triglycerides, LDL, VLDL decreased significantly.

The level of two pro-atherogenic apolipoproteins apolipoprotein B and Lp (a) also decreased markedly. Interestingly, the level of apoA-1, an anti-atherosclerotic apolipoprotein, which has been previously implicated in cholesterol efflux, increased upon EuMil treatment.

Example 4

Figure 5:
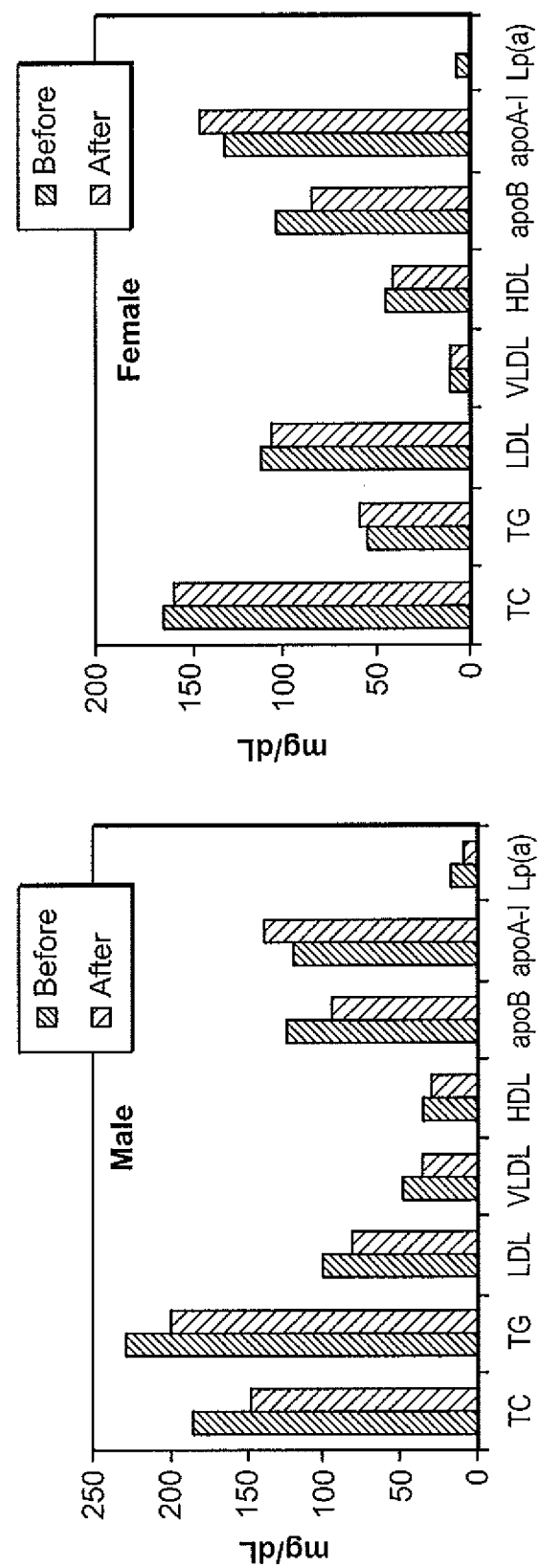
FIG. 5 are two graphs that show the effect of EuMil on lipids, lipoproteins and apolipoproteins in human subjects. A 500 mg capsule of EuMil was swallowed daily for two weeks. Blood was collected by venipuncture and lipid lipoprotein and apoprotein levels were measured using standardized laboratory procedures.
Figure 6:
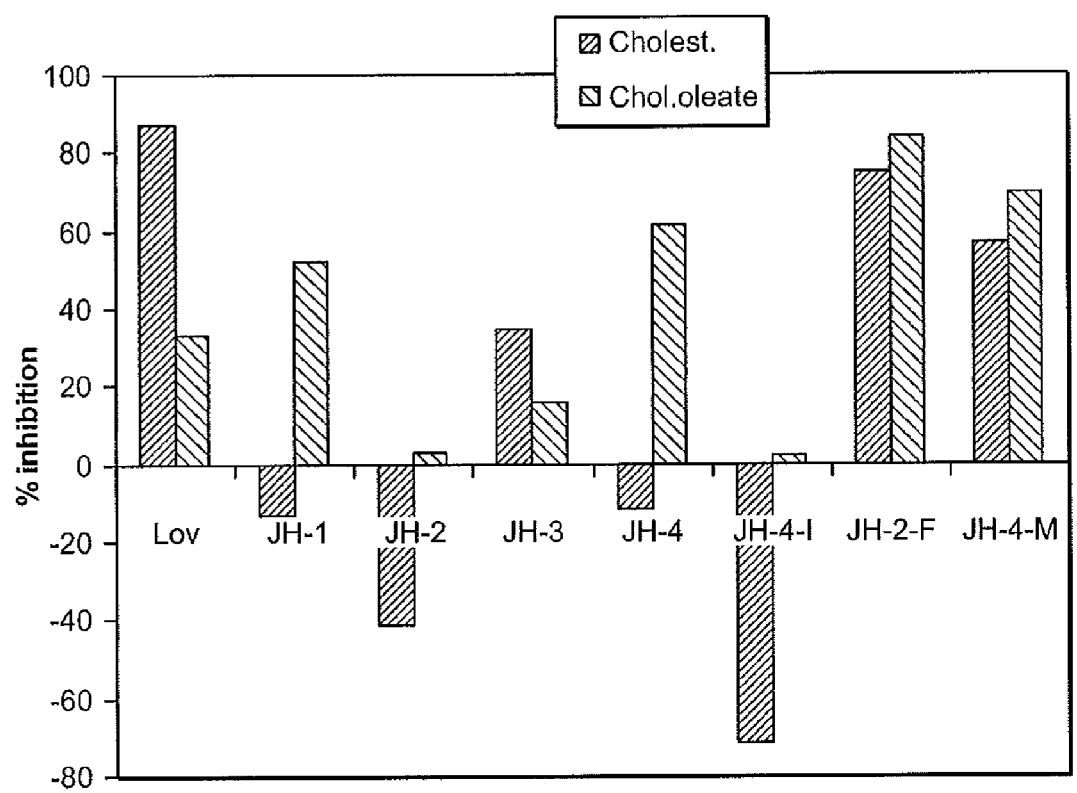
FIG. 6 is a graph that shows the effect of EuMil and its ingredients on cholesterol synthesis in human aortic smooth muscle cells. Cells were incubated with aqueous extracts of *O. sanctum* (JH-1), EO (JH-2), *W. somnifera* (JH-3) and EuMil (JH-4) at concentration 500 µg/ml in medium supplemented with 100 µg/ml oxidized LDL. Cells incubated with 100 µg/ml ox-LDL served as a control. [14C] acetate (2 µCi/ml) was added and incorporation of radioactivity into cholesterol and cholesteryl esters was measured after 24 h of incubation in standard cell culture conditions. Lovastatin (10 µM) plus ox-LDL served as a positive control.

Effect of EuMil and its Major Herbal Ingredients on the Biosynthesis of Cholesterol As shown in FIG. 6, lovastatin markedly decreased the biosynthesis of cholesterol (down to ~20% compared to control) and cholesteryl esters (~50% compared to control). In contrast, crude aqueous extracts of 0. Sanctum (JH-1 crude), EO (JH-2 crude), *W. somnifera* (JH-3 crude) and EuMil (JH-4 crude) marginally inhibited or did not inhibit cholesterol synthesis in ASMC (FIG. 5). However, several of these herbs significantly inhibited cholesteryl ester synthesis. Polyamide was used to remove polymeric tannins from the aqueous extracts of EuMil and its herbal ingredients and the resulting fractions were subjected to cell-based assays.

The results presented herein demonstrate that EuMil, an herbal formulation, can markedly decrease total, free and LDL cholesterol in a rabbit model of hypercholesterolemia and in man via activity of the EO component of EuMil. The data demonstrates that this reversal is, in certain examples, a complete reversal. The results indicate that the hypocholesterolemic activity in EuMil resides within its EO component and lastly, the hypocholesterolemic active compounds identified in EO are derivatives of gallate ester of mucic acid (7, 8 and 9), glucose (4, 5 and 6) and glycerol (3), gallic acid (1) and methyl gallate (2a) or ethyl gallate (2b), depending upon the extraction procedure.

Previous studies have also shown that feeding a diet high in fat and cholesterol induces marked hyperlipidemia in rabbits. This results presented herein are in agreement with these studies. For example, after 2 months of feeding rabbits a high fat and cholesterol diet there was a modest increase in cholesterol which increased ~17 fold after 3 months. Most of this could be attributed to an increase in LDL cholesterol. However, the level of triglyceride remained within the normal range throughout the 3-4 months of experimentation in the EuMil/fat and cholesterol fed rabbits. One important observation in the present study was that in rabbits fed EuMil hypercholesterolemia was almost entirely abrogated, as compared to fat fed rabbits. Feeding rabbits EuMil plus rabbit chow alone did not alter plasma cholesterol and triglyceride levels. Preliminary studies in two normal human subjects demonstrated that the consumption of 500 mg of EuMil daily for 15 days reduced the levels of total and lipoprotein-associated cholesterol and triglycerides. Similarly, the level of two atherogenic lipoproteins (i.e. apolipoprotein B and Lp(a)) also were decreased. The unexpected observation was an increase in the level of apolipoprotein A-I. Apolipoprotein A-I is a major protein component in high density lipoproteins and plays a critical role in "reverse cholesterol transport" by way of facilitating the efflux of cholesterol from peripheral tissues and transporting them back to the liver. These preliminary observations suggest cholesterol efflux as a beneficial biochemical mechanism by which EuMil may lower blood level of cholesterol in addition to inhibition of cholesterol biosynthesis and cholesterol uptake.

Example 5

Measurement of the Effect of Mevalonate on the Intermediary Steps in Cholesterol Biosynthesis Previous studies have shown that the mechanism by which lovastatin inhibits cholesterol biosynthesis involves the inhibition of HMG-CoA reductase activity and this could be bypassed by feeding cells mevalonate [3]. To determine if the hypocholesterolemic molecule derived from EuMil also recruits the above mechanism of inhibition of cholesterol synthesis the following experiment was conducted. Cells were incubated with and without mevalonate (1 mM) and the incorporation of [14C]acetate into various metabolites in the biosynthetic pathway leading to cholesterol synthesis was measured. Briefly, the radiolabeled lipids extracted from cells were dried in nitrogen and subjected to saponification using 1.5 ml of 90% KOH and 1 ml of ethanol. Following incubation for 2 h at 95° C. the samples were extracted with diethyl ether and next, washed with 50% ethanol. The extracts were then subjected to HPTLC using benzene-ethyl acetate (1:5 by volume) as an eluent and each plate was calibrated with squalene, lanosterol, coenzyme Q and cholesterol. Following development, the plates were dried in air and subjected to autoradiography. Finally, the gel areas corresponding to various metabolites were scraped and radioactivity measured by scintillation spectrometry Example 6

Effect of Active Compounds on Cholesterol Biosynthesis and Cholesterol Mass

Figure 8:
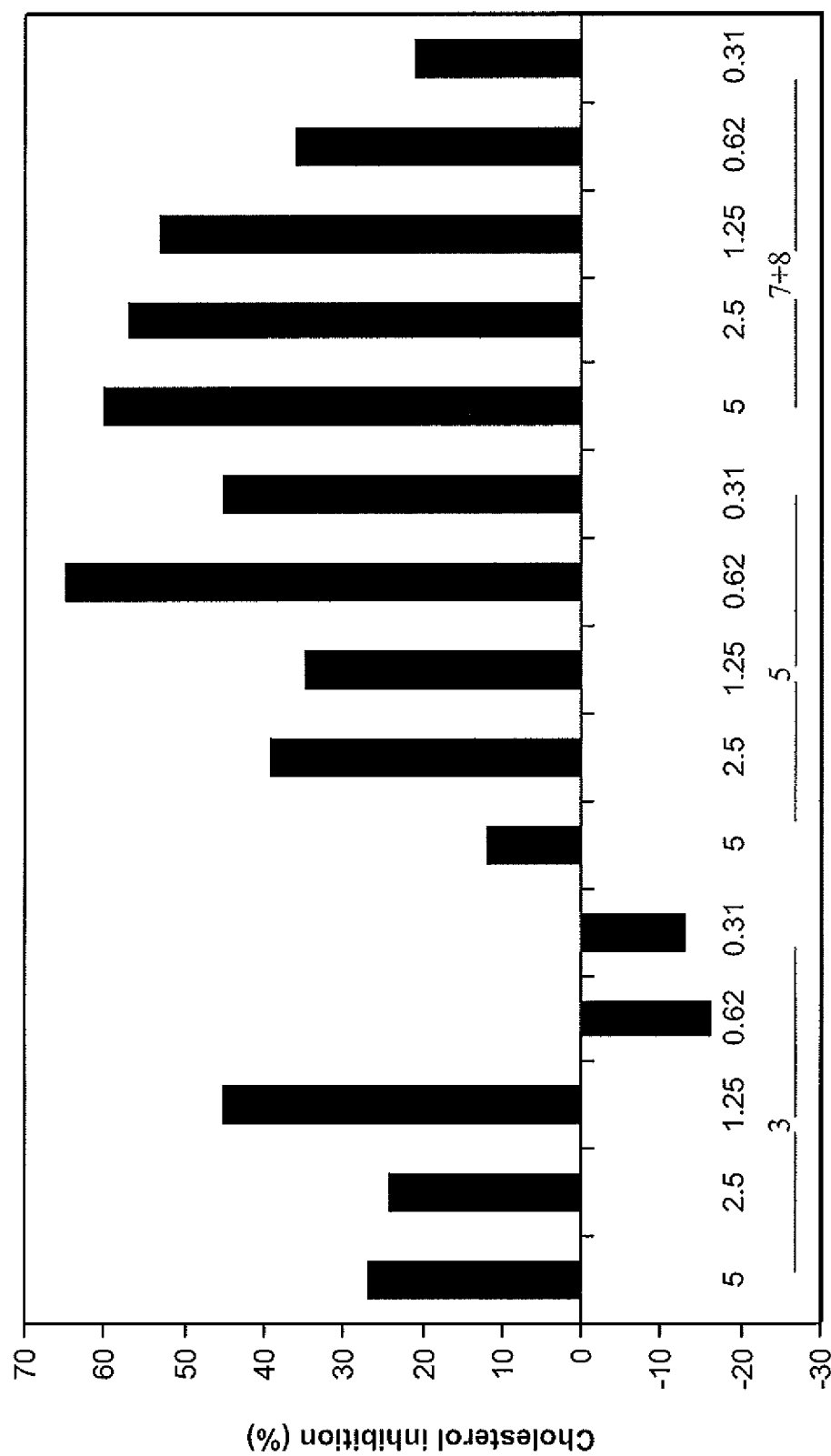
FIG. 8 is a graph showing the effect of active fractions from EO on cholesterol synthesis in human aortic smooth muscle cells.

Next, the effect of the active compounds shown in FIG. 1 and Table 1 on cholesterol biosynthesis was examined. FIG. 8 shows that several fractions derived from EO exhibited a dose-dependent (over a range of 5 µg/ml to 0.31 µg/ml) decrease in cholesterol biosynthesis.

Figure 9:
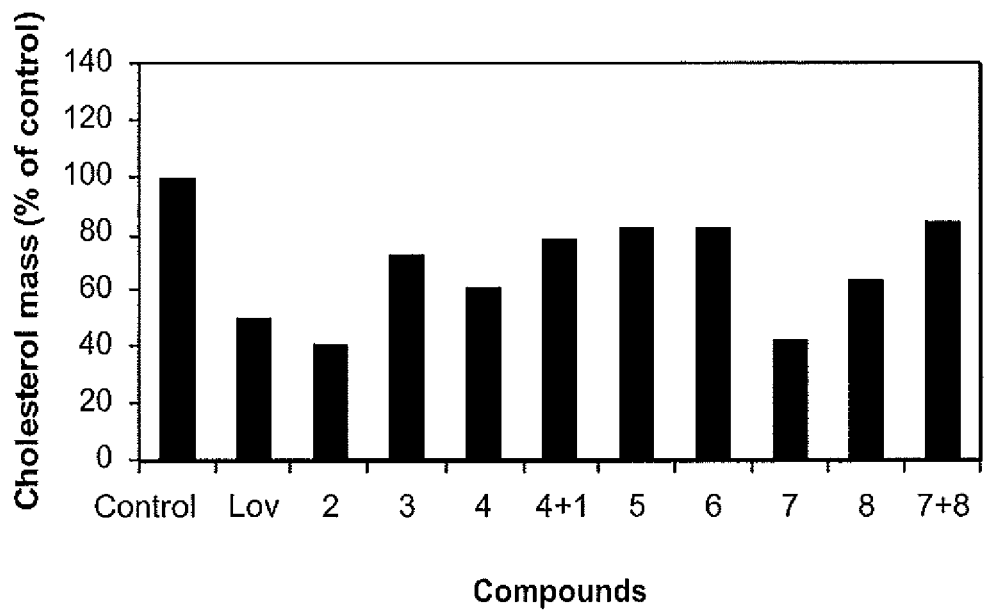
FIG. 9 is a graph showing the effect of active fractions from EO on cholesterol level in human ASMC. Cells were incubated with active fractions (5 µg/ml) and cholesterol mass was determined.

Next, the effect of the active compounds shown in FIG. 1 and Table 1 on cholesterol mass was examined. As shown in FIG. 9, several active fractions derived from EO extract markedly inhibited the cellular mass of cholesterol in ASMC.

Example 7

Effect of Active Fractions on Cholesterol Efflux and Cholesterol Uptake

Figure 10:
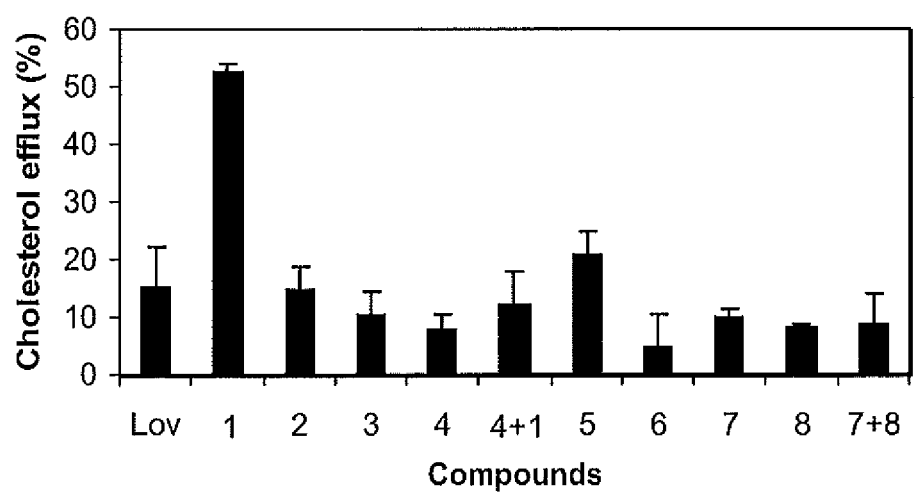
FIG. 10 is a graph showing the effect of active compounds from EO on efflux of cholesterol in human aortic smooth muscle cells. Confluent culture of H-ASMC in 96 well plates was incubated with [3H]cholesterol (5 µCi/ml) for 24 h. Medium was replaced with fresh medium and incubation with herbal fractions was continued for another 24 h. The incorporation of radioactivity into the cells was measured by scintillation spectrometry (N=6).

Next, experiments were performed to examine if the active fractions had an effect on cholesterol efflux and uptake. Several of active fractions significantly increased the efflux of cholesterol from cultured H-ASMC, as shown in FIG. 10. For example, fractions 152, 119V, 137B and 139D markedly induced the efflux of cholesterol from cells. Gallic acid also was effective in inducing cholesterol efflux.

Figure 11:
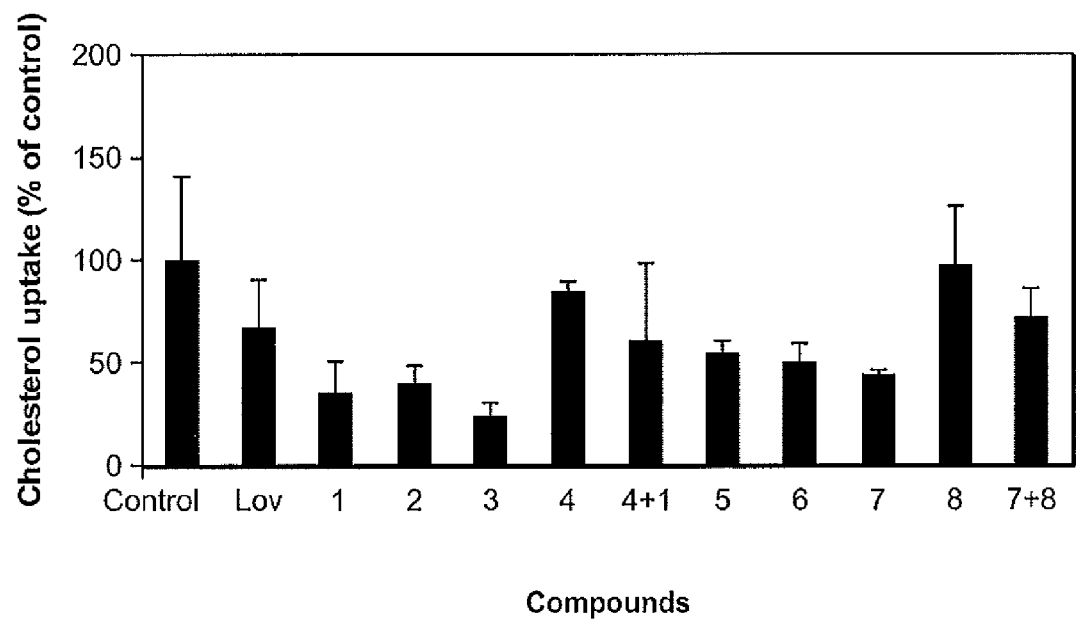
FIG. 11 is a graph showing the effect of active compounds from EO on uptake of cholesterol in human aortic smooth muscle cells. Confluent culture of cells grown in 96 well plates was incubated in serum-free medium with [3H]cholesterol (5 µCi/ml) with and without active fractions. After 24 h the uptake of cholesterol was measured by scintillation spectrometry.

Lovastatin was not effective in inhibition of cholesterol uptake in H-ASMC. However, many active fractions were found to inhibit the uptake of cholesterol, as shown in FIG. 11.

Example 8

Crude Versus Polyamide Treated Extract

Previous Ayurvedic studies have suggested that several herbal mixtures exert their effect in a synergistic manner. Moreover, since EuMil is made up of a mixture of EO, *W. somnifera* and *O. sanctum* (with *Asparagus racemosus* used as a filler for pill preparation), our effort was focused on whether this herbal preparation exerted its hypocholesterolemic effect in a synergistic manner or whether the activity was confined to only one of the above herbal ingredients. Since the crude extracts from EuMil and the herbal preparations above contained large amounts of tanins, the extracts of EuMil and the individual plants were passed through polyamide to remove polymeric tannins, It was found that only the EO and EuMil extracts markedly inhibited cholesterol syntheses in cell-based assays in H-ASMC.

Next, it was decided to look at the difference between the crude extract and the polyamide treated extract. The 25% ethanol extract (115 mg) was eluted through polyamide with 100 ml each of the following solvents: 25%, 50% and 100% ethanol in water. The fractions were combined (35 mg) and analysed by HPLC which is shown in FIG. 12.

Figure 7:
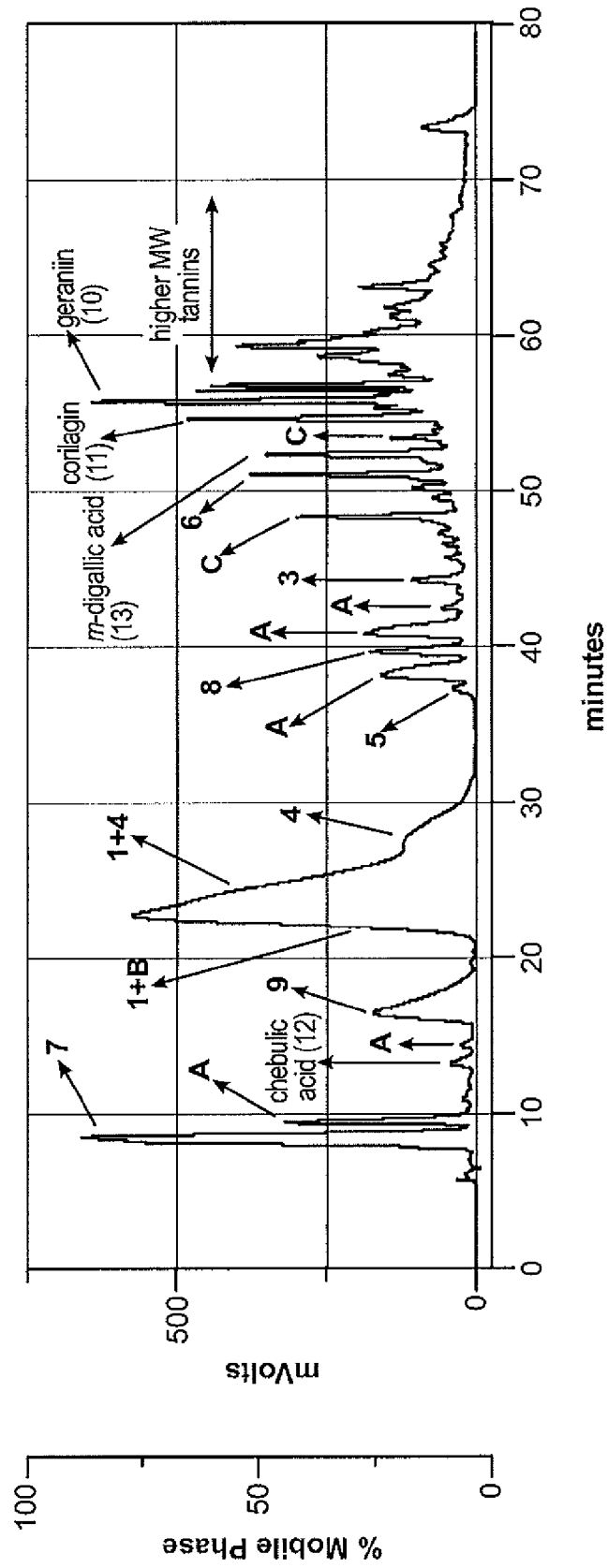
FIG. 7 is a graph that shows typical preparative HPLC chromatogram (UV detection at 210 nM) of the 1:3 ethanol:water extract of EO fruit powder with isolated compounds numbered 1 to 9. Also noted are geraniin numbered 10, corilagin numbered 11, chebulic acid numbered 12 and m-digallic acid numbered 13, mucic acid to gallate derivatives (A), derivatives of the methyl ester of mucic acid gallate (B), derivatives of digalloyl glucose (C) and higher molecular weight tannins Ethylgallate (2b) was not present in the extraction.
Figure 12:
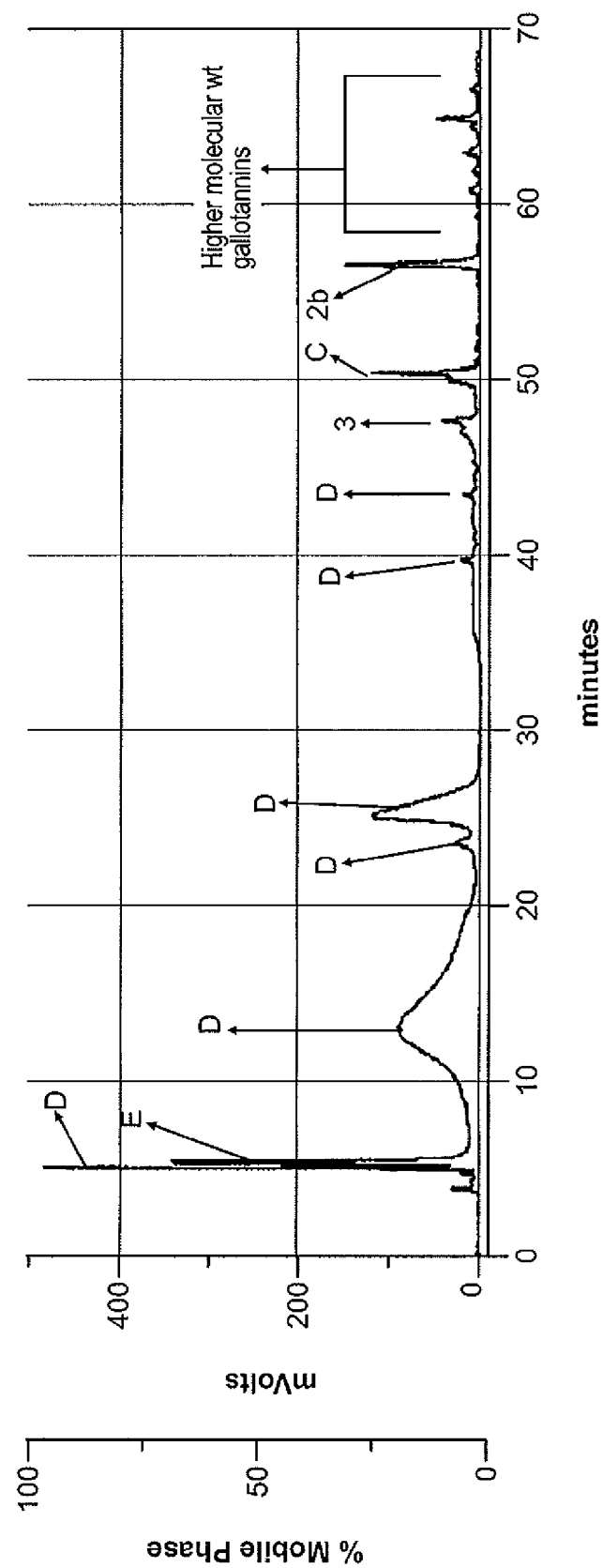
FIG. 12 shows a HPLC chromatogram of the 25% aqueous ethanolic extract of the fruit of *E. officinalis* after polyamide treatment (conditions as used for HPLC) C=derivatives of digalloyl glucose, D=derivatives of galloyl glucose, E=sugar with some galloyl glucose.

Mucic acid and its derivatives and gallic acid were not present after the polyamide treatment by compare the chromatograms of the crude extract (FIG. 7) and polyamide treated extract (FIG. 12). This result was confirmed by MS and NM experiments. Fraction C showed a mass of m/z 484 which is a derivative of compound DGG 16 (6). The rest of the fractions grouped as D, showed a common mass of m/z 332 that corresponded to derivatives of gallic acid attached to one sugar. As discussed previously, ethyl gallate (2b) is an artifact formed during extraction with ethanol. The cholesterol lowering activity shown by the initial polyamide of the crude EO plant extract was due to the presence of enriched amounts of gallic acid derivatives attached to glucose. The latter part showed peaks that correspond to higher molecular weight gallotans present in considerably lower amounts; therefore, polyamide treatment is not an enrichment efficient step as the many of the compounds of interest, especially the mucic acid derivatives, are lost during the process.

The studies presented herein demonstrate that the hypocholesterlemic activity in EuMil resides predominantly with its EO component. The results show that the hypocholesterolemic active compounds are derivatives of gallate ester of mucic acid (7, 8 and 9), glucose (4, 5 and 6) and glycerol (3), gallc acid (1) and methyl gallate (2a) or ethyl gallate (2b) depending on the extraction procedure. The studies using cultured aortic smooth muscle cells reveal that the active compounds lower cholesterol level by a combination of biochemical mechanisms such as inhibition of cholesterol biosynthesis, inhibition of cholesterol uptake and subsequent cholesterol efflux. The studies indicate that the active compounds from EO may recruit multiple mechanisms, unlike the statins, to serve as hypocholesterolemic agents.

As presented herein, the biological/functional studies using the active compounds revealed that gallate had an effect on cell proliferation and apoptosis, while many of the other compounds did not have the same effect. Lovastatin was used as a positive control throughout the studies and also did not appear to inhibit cell proliferation. Thus, most of the active components in EO are not toxic to H-ASMC. Similar observation was made using human umbilical vein endothelial cells and normal human proximal tubular cells (data not shown). In agreement with the cell based assays shown herein that demonstrated the inhibition of cholesterol biosynthesis by active components, the cholesterol mass in these cells was also reduced compared to control. In fact, several active fractions were as good or better then lovastatin in lowering cholesterol level in H-ASMC.

The active compounds lowered cholesterol level by a combination of biochemical mechanisms including, but not limited to, inhibition of cholesterol biosynthesis, inhibition of cholesterol uptake and subsequent cholesterol efflux.

In fact, several active fractions were as good or better then lovastatin in lowering cholesterol level in human ASMC. The results described herein show that several active compounds markedly inhibit the uptake of cholesterol, in particular, methyl gallate (2a). DGG16 (6), GG6 (5) and mucic acid gallate derivatives 7, 8 and 9 were all effective in decreasing cholesterol level in human ASMC. On the other hand, gallate derivatives of mucic acid, methyl gallate and gallate were also very effective in stimulating the efflux of cholesterol from these cells. Previous extensive studies have elaborated the role of ABC-A1 transporters and sterol binding and sterol receptor binding genes/proteins in regulating cholesterol efflux and uptake of cholesterol [7]. It is also well known that the lipid metabolizing genes such as apolipoprotein E (apoE), apolipoprotein B (apoB), cholesteryl ester transporter protein (CETP) and the LDL receptor (LDLR) are targeted by cholesterol lowering drugs such a statins. The results presented herein demonstrate that the active compounds from EO recruits multiple mechanisms in their actions as hypocholesterolemic agents, unlike the statins. Further, the strong antioxidant effect of EO and its related medicinal plant also may play a role in reducing cholesterol [54].

In a recent study it was shown that in ASMC aggregated LDL increased and simvastatin reduced cholesteryl ester accumulation (45). We also observed that in ASMC EuMil markedly reduced ox-LDL induced cholesteryl ester levels. The preliminary in vitro studies suggested that one of the mechanisms by which EuMil reduces cholesterol level may involve inhibition of cholesterol synthesis as well as cholesteryl ester synthesis, without any significant effect on triglyceride level.

Methods and Materials
Cells

Human aortic smooth muscle cells (H-ASMC) were purchased from Cambrex (Walkersville, Md.). All chemicals were purchased from Sigma Chemical Company (St. Louis, Mo.). [3H]Thymidine (5-10 Ci/mmol) and [14C]acetate (50-60 mCi/mmol) were purchased from American Radiolabeled Company (St. Louis, Mo.). High performance thin layer chromatography plates (silica gel 60 Å, Whatman) were purchased from Fisher Scientific (Pittsburgh, Pa.).

EuMil and Plant Material

Dry powder of EuMil herbal formulation, *W. somnifera*, *O. sanctum* and EO were provided by Indian Herbs International, Saharanpur, India. A stock solution of EuMil and its ingredients (1 mg/ml) were dissolved in 12.5% DMSO in water for cell-based assay and immediately used after preparation.

Preparation of Oxidized LDL and its Characterization

Human plasma low density lipoproteins (d 1.022-1.063 g/ml) were prepared from the plasma of normalipidemic controls. This LDL was subjected to oxidation with 10 μM $CuSO_4$ and characterized as described earlier [12].

Incubation of Cells with EuMil/Ingredient Fractions

H-ASMC ($\times 10^5$) were seeded in plastic 6-well trays and grown in smooth muscle cells medium-2 (Cambrex). Incubation was pursued in a water-jacketed incubator with 5% $CO_2$ and 95% air. After the cells reached confluence medium was replaced by plain serum-free medium. Following incubation for 24 h fresh medium, 100 μg/ml ox-LDL and various herbal fractions solubilized in 12.5% DMSO were added. Cells that were incubated with lovastatin (10 μM) served as a positive control in all experiments.

Rabbits and Analysis of Lipids and Lipoproteins

New Zealand white male rabbits (2 months old) were purchased from a local supplier and housed in a sterile/germ free animal facilities for 2-3 days prior to experimentation. Rabbits (5 lbs each), three in each group were fed the following diet for four months. These were: a) a rabbit chow; b) chow plus EuMil (1 gm/kg chow); EuMil plus fat (14% coconut oil and 0.2% cholesterol) and d) 14% coconut oil and 0.2% cholesterol. At one, two, three and four month intervals, the rabbits were bled by venipuncture. Plasma was prepared and lipoproteins (LDL) were isolated by ultracentrifugation. The level of cholesterol, triglycerides and LDL cholesterol was measured employing standardized laboratory procedures at the Johns Hopkins Lipid and Lipoprotein Laboratory using NCEP guidelines.

Human Subjects and Analysis of Lipids and Lipoproteins

Fasting blood from one normal male and one normal female was analyzed for the levels of lipids and lipoproteins. They took one 500 mg pill of EuMil daily for two weeks without any dietary restrictions. Blood was drawn before and after EuMil consumption for 2 weeks and lipid and lipoprotein levels were measured.

Cell-Based Assay:

The cell-based assay was used follow the activity during isolation of the EO fruit powder active principles. The active components were polar in nature and a C-18 HPLC column designed specifically for the isolation of polar compounds was used. The active compounds, which were isolated using preparative HPLC (see FIG. 9 for representative chromatogram), were gallic acid (1), methyl gallate (2a)/ethyl gallate (2b) depending on the extraction solvent used, glycerol-1-gallate (3), glucose-1-gallate (GG1) (4), glucose-6-gallate (GG6) (5), glucose-1,6-digallate (DGG16) (6), mucic acid-2-gallate (7), methyl mucic acid-2-gallate (8) and mucic acid 1,4-lactone 5-gallate (9).

Measurement of Cell Proliferation

Following incubation for 18 h with and without ox-LDL and EuMil/ingredients and lovastatin [3H]thymidine (5 Ci/ml) was added in 96 well dishes and incubation continued for 6 h at 37° C. Next, the cells were washed and the incorporation of [3H]thymidine into DNA was measured employing scintillation spectrometry [12]. The data was calculated as dpm/well. All experimental values were expressed as a percentage of the control values (cells incubated with ox-LDL alone).

Measurement of Apoptosis

ASMC ($\times 10^4$) were seeded on sterile glass cover slips and incubated in the presence/absence of active fractions of EO, lovastatin, ox-LDL for 24 h. Cells were fixed with ethanol-acetic acid (3:1 by volume) at room temperature for 10 min, washed three times with phosphate buffered saline (pH 7.4) and stored at −20° C. Next cell were stained with DAPI (4',6-diamidino-2-phenylindole dihydrochloride) reagent and nuclei were visualized by fluorescence microscopy (Zeiss Axiovert 25).

Measurement of Cholesterol Efflux

For cholesterol efflux studies near confluent cells were labeled with [3H]-cholesterol for 24 h, washed, and incubated for 24 h with the herbal fractions in serum-free DMEM medium. Percentage efflux was calculated by subtracting the radioactive counts in the blank media from the radioactive counts in the presence of an acceptor, and then dividing the result by the sum of the radioactive counts in the medium plus the cell fraction.

Determination of Cholesterol Uptake

Confluent culture of human aortic smooth muscle cells were pre-incubated in serum-free DMEM for 24 h. Next, fresh medium and [3H]cholesterol (5 µCi/ml) plus various herbal compounds were added. Following incubation for 24 h and 48 h, [3H]cholesterol taken up by cell was measured by solubilization in 1 M NaOH and radioactivity measured.

Measurement of the Level of Cholesterol

Following treatment cells were extracted with hexane-isopropanol 3:2 by volume as described above. The pooled extracts were dried in a stream of nitrogen and subjected to measurement of total cholesterol mass using a cholesterol kit (WAKO chemicals, VA) with cholesterol as the standard. The data was expressed as µg cholesterol per mg protein.

Measurement of Cholesterol Biosynthesis in Cultured Cells

Cells were incubated with and without ox-LDL and EuMil/ ingredients and [14C] acetate (1 µCi/ml, 24 h). Next, medium was removed; the monolayers were washed three times with PBS. Cells were extracted with hexane:isopropanol (3:2 by volume, 2×3 ml) at room temperature. The extracts were pooled in glass tubes and total lipid extract dried in nitrogen atmosphere. 1N NaOH (1 ml) was added to each tube to solubilize proteins and the incubated overnight in open air. Next, water (2 ml) was added to the air dried tubes, the contents were mixed and utilized for protein measurement using BCA protein assay kit (Pierce, Rockford, Ill.)

The total lipid extracts were dried in stream of nitrogen, re-suspended in chloroform-methanol (2:1 by volume) and applied on a HPTLC silica gel plate. Standard solutions of cholesterol, monolein, diolein, triolein, fatty acid and cholesteryl oleate (50 µg each) also were applied to the plate. The plates were developed in heptane-ether-acetic acid (85:15:1 by volume). Following development, the plates were dried in air and exposed to an X-ray film for 2-3 days at −800 C. After the films were developed, the HPTLC plates were immersed in iodine vapors to identify the migration of individual neutral lipid molecular species. Gel areas, corresponding to cholesterol were scraped and radioactivity was measured using Beckman liquid scintillation spectrometer. The data was expressed as counts per mg protein. The incorporation of radioactivity in cells incubated with oxidized LDL was considered as 100% (control). All experimental values in cells treated with EuMil/ingredients plus oxidized LDL were expressed as a percentage of the control. All assays were conducted in triplicate.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

REFERENCES

1. Enas A E. Why there is an epidemic of malignant CAD in young Indians. Asia J Clin Cardiol. 1998; 1:43-54.
2. Libby P, Ridker P M, Maseri A. Inflammation and atherosclerosis. Circulation 2002; 105:1135-1143.
3. Goldstein J L, Brown M S, In Schriver et al (eds). The Metabolic Basis of Inherited Disease. McGraw Hill, New York, 1989, pp 1215-1250.
4. Parthasarathy S, Quinn M T, Schwenke D C, Carew T E, Steinberg D. Oxidative modification of beta-very low density lipoprotein. Potential role in monocyte recruitment and foam cell formation. Atherosclerosis 1989; 9:398-404.
5. Randomized trial of cholesterol lowering in 444 patients with coronary heart disease: The Scandinavian Simvastatin Survival Study (4S) Lancet 1994; 334: 1383-1389.
6. Shepherd J, Cobbe S M, Ford I, Isles C G, Lorimer A R, MacFarlane P W, McKillop J H, Packard C J. Prevention of coronary heart disease with pravastatin in men with hypercholesterolemia. West of Scotland Coronary Prevention Study Group. N Engl J. Med. 1995; 333:1301-1307.
7. Yang C, McDonald J, Patel A, Zhang Y, Umetani M, Xu F, Westover E, Covey D, Mangelsdorf D, Cohen J, Hobbs H. Sterol Intermediates from Cholesterol Biosynthetic Pathway as Liver X Receptor Ligands. J Biol. Chem. 2006; 281:27816-27826.
8. Rader D J, Pure E (2005) Lipoprotein, macrophage function, and atherosclerosis: beyond the foam cell? Cell Metab. 1:223-30
9. Muruganandam A V, Kumar V, Bhattacharya S K. Effect of poly herbal formulation, EuMil, on chronic stress-induced homeostatic perturbations in rats. Indian J Exp Biol. 2002; 40:1151-1160.
10. Bhattacharya A, Muruganandam A V, Kumar V, Bhattacharya S K. Effect of poly herbal formulation, EuMil, on neurochemical perturbations induced by chronic stress. Indian J Exp Biol. 2002; 40:1161-1163.
11. Chauhan S K, Singh B P, Tuago A, Agrawal S, Accelerated stability studies of a polyherbal preparation (EuMil) capsule. Ind J Pharm Sci. 2000; 62: 181-184.
12. Nadkarni, A. K. (1976) In: Indian: Materia Medica 1954, revised edn. Bombay Popular Prakasam, Bombay.
13. Unander D W, Webster G L, Blumberg B S. Related Records of usage or assays in *Phyllanthus* (Euphorbiaceae). Subgenera *Isocladus, Kirganelia, Cicca* and *Embilica*. J. Ethnopharmacol. 1990; 30:233-264.
14. Calixto J B, Santos A R S, Cechiel Filho V, Yunes R A. A review of the plants of the genus *Phyllanthus*: their chemistry, pharmacology, and therapeutic potential. Med Res Rev. 1998; 18:225-258.
15. Scartezzini P, Antognoni F, Raggi M A, Poli F, Sabbioni C. Vitamin C content and antioxidant activity of the fruit and of the Ayurvedic preparation of *Embilica officinalis* Gaertn. J. Ethnopharmacoi. 2006; 104:113-118.
16. Ghosal S, Tripathi V K, Chauhan S. Active constituents of *Embilica officinalis* Part I—The chemistry and antioxidative effects of two new hydrolysable tannins, embilicanin A and B. IndJChem, 1996; 35: 941-948.
17. Nonaka G, Nishioka I. Tannins and related compounds. X Rhubarb (2): Isolation and Structures of glycerol gallate, gallic acid glucoside gallates, galloyl glucoses and Isolindleyin. Chem. Pharm Bull. 1983; 31:1652-1658.

18. Saijo R, Nokaka G, Nishioka i. Gallc acid esters of bergenin and norbergenin from *Mallotus japonicus*. Phytochemistry. 1990; 29:267-270.
19. Saijo R, Nokaka G, Nishioka I. Tannins and related compounds. LXXIV. Isolation and characterization of five new hydrolyzable tannins from the bark of *Mallotus japonicus*. Chem Pharm Bull (Tokyo). 1989; 37:2063-2070.
20. Zhang Y J, Nagao T, Tanaka T, Yang C R, Okabe H, Kouno I. Antiproliferative activity of the main constituents from *Phyllanthus embilica*. Biol Pharm Bull. 2004; 27:251-255.
21. Duan W, Yu Y, Zhang L. Antiatherogenic effects of *Phyllanthus embilica* associated with corilagin and its analogue. Yakugaku Zasshi. 2005; 125:587-591.
22. Zhang Y J, Tanaka T, Yang C R, Kouno I. New phenolic constituents from the fruit juice of *Phyllanthus embilica*. Chem Pharm Bull (Tokyo). 2001; 49:537-540.
23. Quinn M T, Parthasarathy S, Fong L G, Steinberg D. Oxidatively modified low density lipoprotein: a potential role in recruitment and retention of monocyte/macrophages during atherogenesis. Proc Natl Acad Sci USA. 1987; 84:2995-2998.
24. Berliner J A, Navab M, Fogelman A M, Frank J S, Demer L L, Edwards P A, Watson A D, Lusis A J. Atherosclerosis: basic mechanisms. Oxidation, inflammation, and genetics. Circulation. 1995; 91:2488-2496.
25. Chatterjee B J, Subbanagounder G G, Bhunia A, Koh S. Identification of a biologically active component in minimally oxidized low density lipoprotein (MM-LDL) responsible for aortic smooth muscle cell proliferation. Glycoconjugates J. 2004; 20:331-338.
26. Benny A. Composition to enhance HDL cholesterol and to decrease intima-media thickening in animals and humans and a method for its preparation. US Patent Application US200528191 A1.
27. Benny A. A Process and technique to elevate serum high density lipoprotein. World Patent Application WO2004078190 A1.
28. Tariq M, Hussain S J, Asif M, Jahan M. Protective effect of fruit extracts of *Embilica officinalis* (Gaertn). & *Terminalia belerica* (Roxb.) in experimental myocardial necrosis in rats. Indian J Exp Biol. 1977; 15:485-486.
29. Mishra M, Pathak U N, Khan A B. *Embilica officinalis* Gaertn and serum cholesterol level in experimental rabbits. Br J Exp Pathol. 1981; 62:526-528.
30. Thakur C P, Mandal K. Effect of *Embilica officinalis* on cholesterol-induced atherosclerosis in rabbits. Indian J Med. Res. 1984; 79:142-146.
31. Thakur C P. *Embilica officinalis* reduces serum, aortic and hepatic cholesterol in rabbits. Experientia. 1985; 41:423-424.
32. Thakur C P, Thakur B, Singh S, Sinha P K, Sinha S K. The Ayurvedic medicines Hartai, Amala and Babra reduce cholesterol-induced atherosclerosis in rabbits. Int J CardioL 1988; 21:167-175.
33. Jacob A, Pandey M, Kapoor S, Saroja R. Effect of the Indian gooseberry (amala) on serum cholesterol levels in men aged 35-55 years. Eur J Clin Nutr. 1988; 42:939-944.
34. Mathur R, Sharma A, Dixit V P, Varma M. Hypolipidaemic effect of fruit juice of *Embilica officinalis* in cholesterol-fed rabbits. J. Ethnopharmacol. 1996; 50:61-68.
35. Anila L, Vijayalakshmi N R. Flavonoids from *Embilica officinalis* and *Mangifera indica*—effectiveness for dyslipidemia. J. Ethnopharmacol. 2002, 79–81-87.
36. Anila L, Vijayalakshmi N R. Beneficial effects of flavonoids from *Sesamum indicum*, *Embilica officinalis* and *Momordica charantia*. Phytother Res. 2000, 14, 592-595.
37. Augusti K T, Arathy S L, Asha R, Ramakrishanan J, Zaira J, Lekha V, Smitha S, Vijayasree V M. A comparative study on the beneficial effects of garlic (*Allium sativum* Linn), amla (*Embilica Offcinalis* Gaert) and onion (*Allum cepa* Linn) on the hyperlipidemia induced by butter fat and beef fat in rats. Indian J Exp Bioi. 2001; 39:760-766.
38. Babu P S, Stanely Mainzen Prince P. Antihyperglycaemic and antioxidant effect of hyponidd, an ayurvedic herbomineral formulation in streptozotocin-induced diabetic rats, Pharm Pharmacol. 2004; 56:1435-1442.
39. Suryanarayana P, Kumar P A, Saraswat M, Petrash J M, Reddy G B. Inhibition of aldose reductase by tannoid principles of *Embilica officinalis*: implications for the prevention of sugar cataract. Mol. Vis. 2004; 10:148-154.
40. Rao T P, Sakaguchi N, Juneja L R, Wada E, Yokozawa T. Amla (*Embilica officinalis Gaertn.*) extracts reduce oxidative stress in streptozotocin-induced diabetic rats. J Med Food. 2005; 8:362-368.
41. Kim H J, Yokozawa T, Kim H Y, Tohda C, Rao T P, Juneja L R. Influence of amla (*Embilica officinalis Gaertn.*) on hypercholesterolemia and lipid peroxidation in cholesterol-fed rats. J Nutr Sci Vitaminol. 2005; 51:413-418.
42. Veena K, Shanthi P, Sachdanandam P. The biochemical alterations following administration of Kalpaamruthaa and Semecarpus anacardium in mammary carcinoma. Chem Bioi Interact. 2006; 161:69-78.
43. Tomohiko K, Teetamu P R Obesity inhibition Composition, Japanese Patent Application JP2006008527.
44. Noboru S, Teetamu P R, Takako Y. Composition for Controlling Diabetic Nephropathy, Japanese Patent Application JP2006008528.
45. Llorente-Cortes V, Martinez-Gonzalez J, Badimon L. Differential cholesteryl ester Accumulation in two human vascular smooth muscle cell subpopulations exposed to Aggregated LDL: effect of PDGF-stimulation and HMG-CoA reductae inhibition Atherosclerosis 1999; 144:335-342.
46. Oliveira M V, Badia E, Carbonneau M A, Grimaldi P, Fouret G, Lauret C, Leger C L. Potential anti-atherogenic cell action of the naturally occurring 4-O-methyl derivative of gallic acid on Ang II-treated macrophages. FEBS Lett. 2004; 577:239-244.
47. Dufour C, Da Silva E, Potier P, Queneau Y, Dangles O. Gallic esters of sucrose as efficient radical scavengers in lipid peroxidation. J Agric Food Chem. 2002; 50:3425-3430.
48. Murase T, Kume N, Hase T, Shibuya Y, Nishizawa Y, Tomikitsu I, Kita T. Gallates inhibit cytokine-induced nuclear translocation of NF-kB and expression of leukocyte adhesion molecules in vascular endothelial cells. Arterioscler Thromb Vase Biol. 1999; 19:1412-1420.
49. Abe I, Seki T, Noguchi H. Potent and selective inhibition of squalene epoxidase by synthetic galloyl esters Biochem Biophys Res Commun. 2000; 270:137-140.
50. Bok S H, Jeong T S, Choi M S, Hyun B H, Lee C H, Choi Y K, Bae K H, Park Y B, Kwon Y K, Moon S S et al (2000) Method for preventing or treating elevated blood lipid level-related diseases by administering natural phenolic compounds. U.S. Pat. No. 6,133,311.
51. Cheng J T, Hsu F L (1993) Tannin derivatives and their use for treatment of hypertension, U.S. Pat. No. 5,266,319.
52. Park J K, Suk K H, Cho H J, Hoon L C, Hoon K Y, Kyu S J (1998) Cholesterol lowering pharmaceutical composition. WO9842350.
53. Cash W D (1974) Production of an hypertensive effect with esters of gallic acid. U.S. Pat. No. 3,784,695.

54. Sabu M C, Kuttan R. Anti-diabetic activity of medicinal plants and its relationship with their antioxidant property. J. Ethnopharmacol. 2002; 81:155-160.
55. Okuda T, Yoshida T, Hatano T. Constituents of *Geranium thunbergii* Sieb. Et Zucc. Part 12. Hydrated stereo structure and equilibration of geraniin. J Chem Soc, Perkin Trans 1. 1982; 9-14.
56. Zhang Y J, Abe T, Tanaka T, Yang C R, Kouno I. Phyllanemblinins A-F, new ellagitannins from *Phyllanthus embilica*. J Nat Prod 2001; 64:1527-32.
57. Nawwar M A, Hussein S A M, Merfort I. NMR spectral analysis of polyphenols from *Punica granatum*. Phytochemistry 1995; 36: 793-798
58. Yoshida T, Okuda T, Koga T, Toh N. Absolute configurations of chebulic, chebulinic and chebulagic acid. Chem Pharm Bull (Tokyo). 1982; 30: 2655-2658.
59. Nishizawa M, Yamagishi T Tannins and related compounds Par 5. Isolation and characterization of polygalloylglucoses from Chinese gallotan. J Chem Soc Perkin Trans 1. 1982; 2963-2968.

What is claimed is:

1. A method for treating inflammation in a subject comprising
    identifying a subject suffering from inflammation; and
    administering to the subject a composition consisting of an effective amount of two or more gallic acid derivatives isolated from *Emblica officinalis*, wherein the two or more gallic acid derivatives are selected from the group consisting of: glucose-6-gallate (GG6), glycerol-1-gallate, glucose-1-gallate (GG1), glucose-1,6-digallate (DGG16), mucic acid-2-gallate, 1-methyl mucate-2-gallate, mucic acid 1,4-lactone 5-gallate, corilagin, chebulic acid, and m-digallic acid with minor p-digallic acid, thereby treating inflammation in the subject.

2. A method for treating a stress response in a subject comprising
    identifying a subject suffering from inflammation; and
    administering to the subject a composition consisting of an effective amount of two or more gallic acid derivatives isolated from *Emblica officinalis*, wherein the two or more gallic acid derivatives are selected from the group consisting of: glucose-6-gallate (GG6), glycerol-1-gallate, glucose-1-gallate (GG1), glucose-1,6-digallate (DGG16), mucic acid-2-gallate, 1-methyl mucate-2-gallate, mucic acid 1,4-lactone 5-gallate, chebulic acid, and m-digallic acid with minor p-digallic acid, thereby treating a stress response in the subject.

3. The method of claim 1, wherein the two or more gallic acid derivatives is administered as a nutraceutical.

4. A method for treating inflammation in a subject comprising
    identifying a subject suffering from inflammation; and
    administering to the subject a composition comprising an effective amount of two or more gallic acid derivatives isolated from *Emblica officinalis*, wherein the two or more gallic acid derivatives are selected from the group consisting of: glucose-6-gallate (GG6), glycerol-1-gallate, glucose-1-gallate (GG1), glucose-1,6-digallate (DGG16), mucic acid-2-gallate, 1-methyl mucate-2-gallate, mucic acid 1,4-lactone 5-gallate, chebulic acid, and m-digallic acid with minor p-digallic acid, and one or more second agents, wherein the composition does not contain extracts isolated from *Withania somnifera* or *Ocimum sanctum*, thereby treating inflammation in the subject.

5. The method of claim 4, wherein the one or more second agents is a therapeutic agent.

6. The method of claim 5, wherein the therapeutic agent is selected from the group consisting of: inhibitors of cholesterol metabolism, inhibitors of triglyceride synthesis, beta blockers, diuretics, inhibitors of platelet aggregation, angiogenesis inhibitors, arthritis medication, toxins, anti-inflammatory agents.

7. The method of claim 5, wherein the therapeutic agent is attached to the gallic acid derivative by a covalent linkage.

8. The method of claim 5, wherein the therapeutic agent is administered in combination with the one or more gallic acid derivatives.

9. The method of claim 1, wherein the subject is a mammal.

10. The method of claim 9, wherein the mammal is a human.

11. The method of claim 1, wherein the two or more gallic acid derivatives are selected from the group consisting of: glycerol-1-gallate and glucose-6-gallate (GG6), glycerol-1-gallate and mucic acid-2-gallate, GG6 and mucic acid-2-gallate, and glycerol-1-gallate and GG6 and mucic acid-2-gallate.

12. The method of claim 2, wherein the two or more gallic acid derivatives are selected from the group consisting of: glycerol-1-gallate and glucose-6-gallate (GG6), glycerol-1-gallate and mucic acid-2-gallate, GG6 and mucic acid-2-gallate, and glycerol-1-gallate and GG6 and mucic acid-2-gallate.

13. The method of claim 4, wherein the two or more gallic acid derivatives are selected from the group consisting of: glycerol-1-gallate and glucose-6-gallate (GG6), glycerol-1-gallate and mucic acid-2-gallate, GG6 and mucic acid-2-gallate, and glycerol-1-gallate and GG6 and mucic acid-2-gallate.

* * * * *